United States Patent
Nissim et al.

(10) Patent No.: US 10,300,451 B2
(45) Date of Patent: May 28, 2019

(54) METHOD FOR GENERATING AN AFFINITY REAGENT LIBRARY

(71) Applicant: Queen Mary University of London, London (GB)

(72) Inventors: Ahuva Nissim, London (GB); John Marshall, London (GB); Mark Howard, Kent (GB)

(73) Assignees: Queen Mary University of London, London (GB); University of Kent, Canterbury, Kent (GB)

( * ) Notice: Subject to any disclaimer, the term of this patent is extended or adjusted under 35 U.S.C. 154(b) by 334 days.

(21) Appl. No.: 14/899,880

(22) PCT Filed: Jun. 19, 2014

(86) PCT No.: PCT/GB2014/051881
§ 371 (c)(1),
(2) Date: Dec. 18, 2015

(87) PCT Pub. No.: WO2014/202984
PCT Pub. Date: Dec. 24, 2014

(65) Prior Publication Data
US 2016/0144331 A1 May 26, 2016

(30) Foreign Application Priority Data
Jun. 20, 2013 (GB) .................... 1311031.7

(51) Int. Cl.
*C07K 16/28* (2006.01)
*B01J 19/00* (2006.01)
*C07K 16/18* (2006.01)

(52) U.S. Cl.
CPC .......... *B01J 19/0046* (2013.01); *C07K 16/18* (2013.01); *C07K 16/2839* (2013.01); *B01J 2219/00725* (2013.01); *C07K 2317/565* (2013.01); *C07K 2317/76* (2013.01); *C07K 2317/77* (2013.01)

(58) Field of Classification Search
None
See application file for complete search history.

(56) References Cited

U.S. PATENT DOCUMENTS

| 5,831,012 A * | 11/1998 | Nilsson | C07K 14/31 435/6.16 |
| 2008/0267981 A1* | 10/2008 | Janda | C07D 403/06 424/181.1 |
| 2009/0123370 A1* | 5/2009 | Howard | C07K 7/08 424/1.69 |

FOREIGN PATENT DOCUMENTS

WO   WO-2002/048189 A2   6/2002

OTHER PUBLICATIONS

JMB 382:385-401 (Year: 2008).*
Janda PNAS 91:10779-85 (Year: 1994).*
Hauser et al., Use of a peptide derived from foot-and-mouth disease virus for the onoinvasive imaging of human cancer: Generation and valuation of 4-[18F]fluorobenzoyl A20FMDV2 for in vivo imaging of integrin alphavbeta6 expression with position emission tomography. *Cancer Res.* 67(16): 7833-40 (2007).
Li et al., Synthesis and characterization of a high-affinity alphavbeta6-specific ligand for in vitro and in vivo applications. *Molec. Cancer Ther.* 8(5): 1239-49 (2009).
Van Den Beucken et al., Building novel binding ligands to B7.1 and B7.2 based on human antibody single variable light chain domains. *J. Molec. Biol.* 310(3): 591-601 (2001).
Whitby et al. Comprehensive peptidomimetic libraries targeting protein-protein interactions. *Acc. Chem. Res.* 45(10): 1698-709 (2012).
Hazelbag, et al., "Overexpression of the αvβ6 integrin in cervical squamous cell carcinoma is a prognostic factor for decreased survival", Journal of Pathology, 212:316-324 (May 2007).

* cited by examiner

*Primary Examiner* — Christopher M Gross
(74) *Attorney, Agent, or Firm* — Marshall, Gerstein & Borun LLP

(57) ABSTRACT

The present disclosure provides a method for generating an affinity reagent library against a target protein which interacts with a ligand, which comprises the following steps; •i) determining one or more structural element(s) of the ligand which are involved in ligand: target protein interaction; •ii) producing a library of peptides which retain these structural element(s); and •iii) grafting each peptide from the library of peptides into a portion of the affinity reagent molecule such that it may interact with the target protein, in order to produce an affinity reagent library.

17 Claims, 9 Drawing Sheets

Specification includes a Sequence Listing.

a. Sequence and NMR determined structure of A20FMDV $N_1A_2V_3P_4N_5L_6R_7G_8D_9L_{10}Q_{11}V_{12}L_{13}A_{14}Q_{15}K_{16}V_{17}A_{18}R_{19}T_{20}$ b. Algorithm for generation of α-helix library $E_1P_2R_3G_4 D_5L_6X_7X_8L_9A_{10}A_{11}R_{12}Z_{13}K_{14}R_{15}Z_{16}F_{17}N_{18}E_{19}Z_{20}L_{21}A_{22}Z_{23}L_{24}Q_{25}E_{26}K_{27}G_{28}I_{29}$ $E_1P_2R_3G_4 D_5L_6X_7X_8L_9A_{10}A_{11}R_{12}Z_{13}K_{14}R_{15}Z_{16}F_{17}N_{18}E_{19}Z_{20}L_{21}A_{22}Z_{23}L_{24}Q_{25}E_{26}K_{27}G_{28}I_{29}$ c. Algorithm for generation of 3₁₀-helix library $E_1P_2R_3G_4 D_5L_6X_7X_8L_9A_{10}A_{11}Z_{12}L_{13}K_{14}Z_{15}E_{16}F_{17}Z_{18}E_{19}N_{20}Z_{21}L_{22}A_{23}Z_{24}L_{25}Q_{26}E_{27}K_{28}G_{29}I_{30}$ $L_6, Z_{12}, Z_{15}, Z_{18}, Z_{21}, Z_{24}$ $A_{11}, K_{14}, F_{17}, N_{20}, A_{23}$ $A_{10}, L_{13}, E_{16}, L_{22}, L_{25}$

FIG. 1 a. D25p: EPRGDLRTLAAREKRNFNETLARLQEKGI b. D34p: QPRGDLRELAARSEAQLQEKGI

ମETHOD FOR GENERATING AN AFFINITY REAGENT LIBRARY

FIELD OF THE INVENTION

The invention relates to a method for generating an affinity reagent library against a target protein.

BACKGROUND TO THE INVENTION

Antibody discovery programmes have become an important source of both therapeutic biomolecules and research reagents. However, the process of obtaining specific antibodies, particularly for use in therapy, remains time consuming and empirical.

The genetic basis for the structural diversity of antibodies is partially encoded in the germ line, but is also the result of stochastic genetic events, including chromosomal rearrangements, nontemplated nucleotide insertions and somatic hypermutation. The majority of this diversity is localised to the variable heavy ($V_H$) and variable light ($V_L$) antibody regions, and principally to the complementarity-determining regions (CDRs), which are the six-peptide loops that protrude from the variable domain framework to form the antigen-combining surface of the antibody molecule. Three CDR loops are contributed by the heavy chain ($V_H$—CDR1, $V_H$—CDR2 and $V_H$—CDR3) and three by the light chain ($V_L$—CDR1, $V_L$—CDR2 and $V_L$—CDR3). CDR1 and CDR2 are encoded in the germ line, and are thus relatively constrained in their diversity. $V_L$—CDR3 is formed during the recombination of the light chain V and J genomic fragments whilst $V_H$-CDR3 is formed by two consecutive genetic rearrangements, first between D and J and then between V and DJ. This rearrangement is additionally accompanied by the addition of non-templated nucleotides, making $V_H$-CDR3 the source of most naturally occurring antibody diversity.

The use of combinatorial phage display single chain fragment variable (scFv) libraries for generation of therapeutic antibodies is well established and has resulted in clinically valuable reagents. ScFv libraries are made from immune or naïve B cells or as synthetic libraries where antibody $V_H$ and $V_L$ gene segments are rearranged in vitro with synthetic CDRs coding for random sequences of varying lengths. A drawback of the above method, however, is that target specific scFv binders can bind to any epitopes on the target antigen. In the case of development of affinity reagents for therapeutic applications there is a need to develop a more robust platform technology that is able to develop reagents that have therapeutic efficacy, and thus bind to the active moiety of the target antigen.

DESCRIPTION OF THE FIGURES

FIG. 1—Schematic of library design.

The amino acid sequence and NMR solution structure of A20FMDV2 with a hairpin structure with RGD at the tip of the turn followed by a C-terminal helix is shown (a). From these data two algorithms were designed of $V_H$-CDR3 encoding a hairpin containing at its turn, an RGD motif, followed by a C-terminal α-helix (b) or a $3_{10}$-helix (c); amino acid positions that are available for randomisation are highlighted (X and Z shown in blue and red, respectively).

Figure 2:
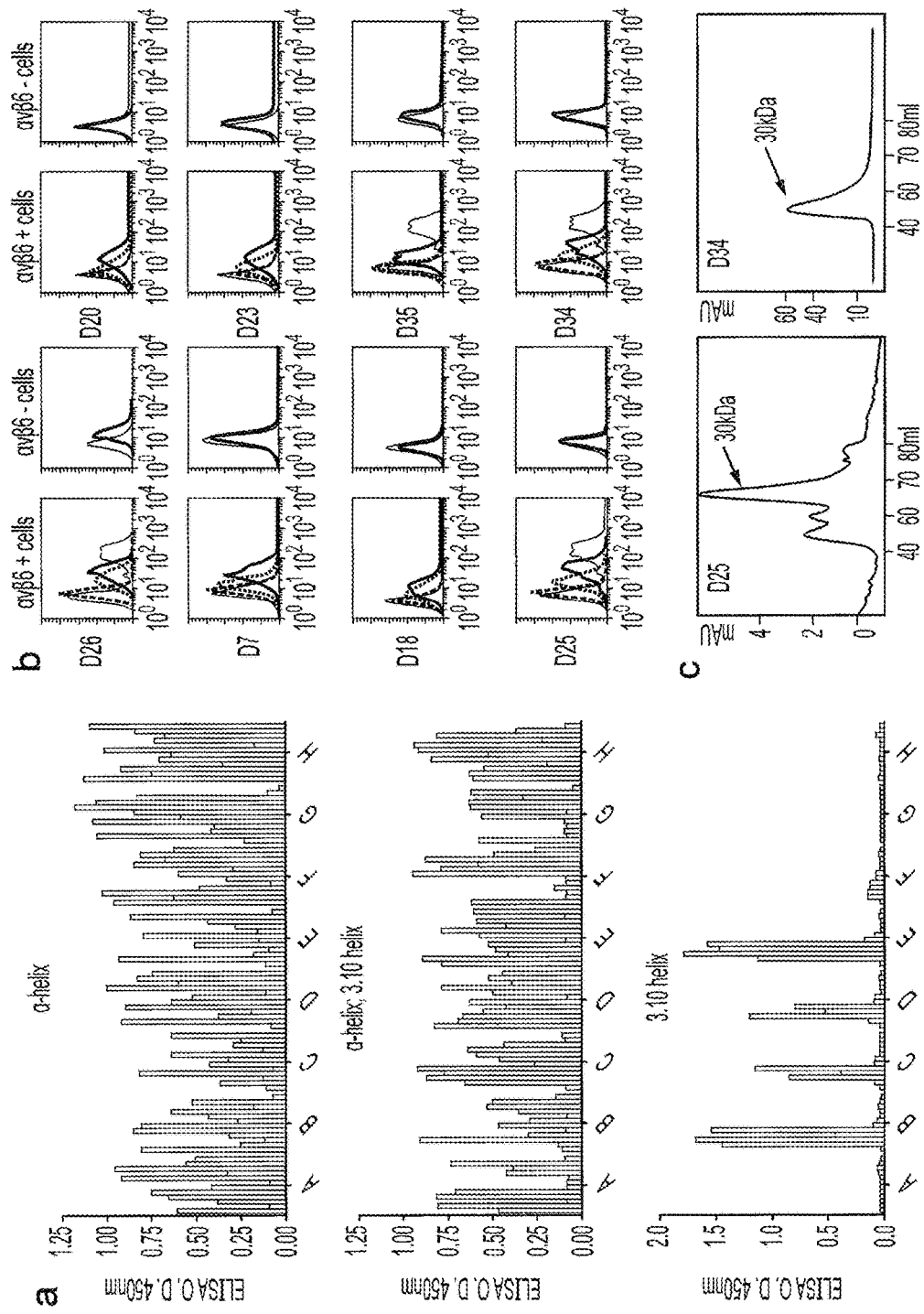

FIG. 2—Screening of phage clones.

a) Representative ELISA screening for scFv clones binders, testing 96 clones in each library. Bacterial supernatants were added to 5 μg/ml recombinant αVβ6 immobilized onto ELISA plate and then probed with mouse anti-Myc antibody followed by anti-mouse-HRP. Libraries were screened alone or mixed together. b) All unique strong binders were tested at 100 (red histogram), 10 (orange histogram) and 1 (green histogram) μg/ml for binding cellular αVβ6 by flow cytometry. The αvβ6-specific antibody 10D5 (light grey histogram) and the control IgG (dark grey histogram) are also shown. c) The size-exclusion chromatography profile of purified of D25scFv and D34scFv.

Figure 3:
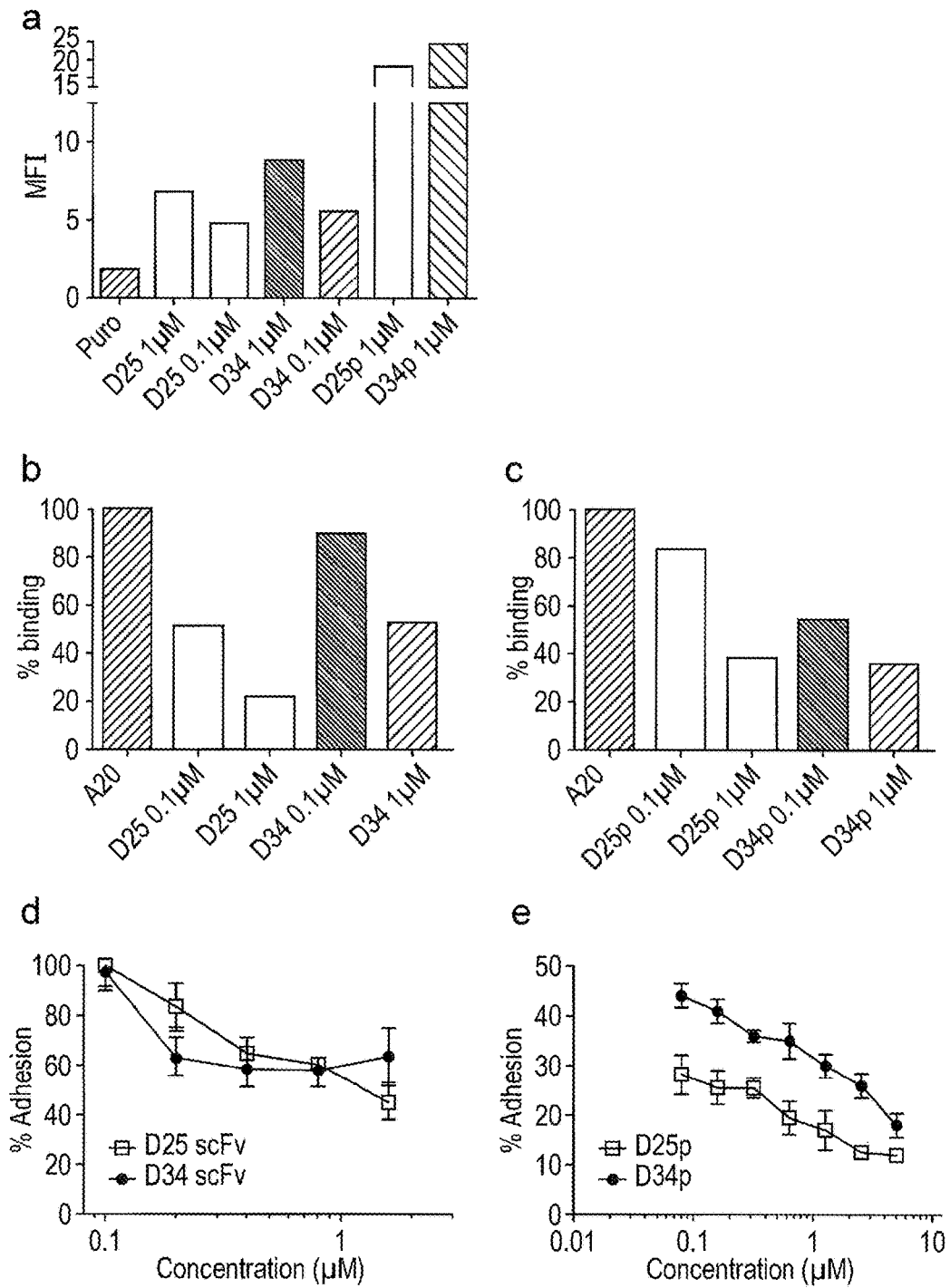

FIG. 3—Cellular αVβ6 binding efficacy of D25scFv, D34scFv, D25p and D34p.

(a) Binding to A375P β6 demonstrated by flow cytometry. The mean florescence intensity (MFI) values recorded from representative experiments are shown. A375Puro cells were used for the negative control (puro). Dose-dependent inhibition of the αvfβ6 specific binding of A20FMDV2 (A20) with (b) both D25 (D25scFv) and D34 (D34scFv) and (c) D25p and D34p peptides. A20FMDV2 binding is expressed as a percentage of the MFI value detected in the absence of scFv or peptide inhibitors. αvβ6-dependent adhesion to fibronectin was inhibited by (d) D25scFv and D34scFv and (e) D25p and D34p (p=0.0156).

Figure 4:
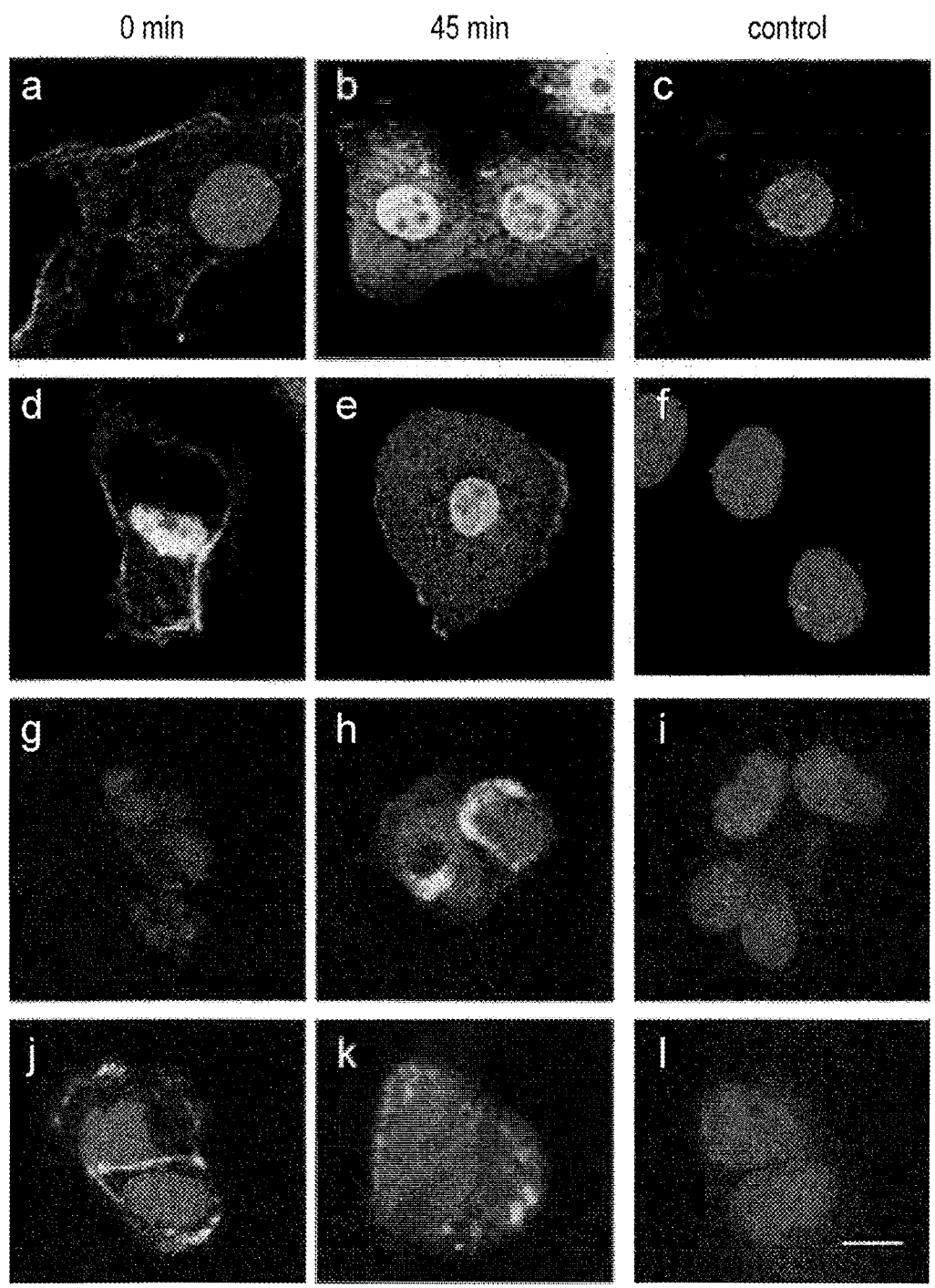

FIG. 4—Internalisation of D25scFv, D34 scFv, D25p and D34p.

Intracellular internalisation of D25scFv (a,b) and D34scFv (d,e) at 0 and 45 mins in αVβ6-expressing cells but not in αVβ6-negative cells. For the negative controls, the primary scFv was omitted (c,f). Internalisation of D25p (g, h) and D34p (j,k) in αVβ6-expressing cells at 0 and 45 mins. In contrast to scFvs nuclear localisation was not seen with the peptides. No peptide internalization was observed in in the αVβ6-negative cells (i,l). The scale bar shown represents 20 μm.

Figure 5:
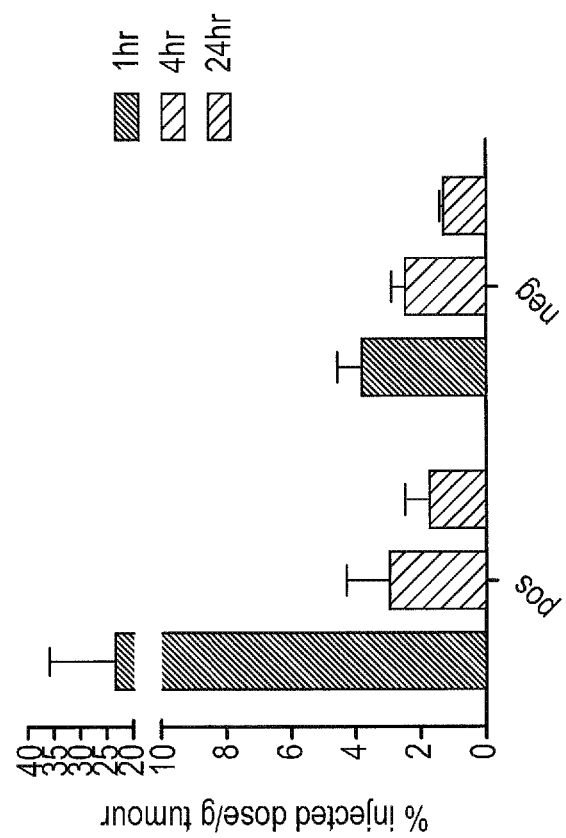
Figure 5:
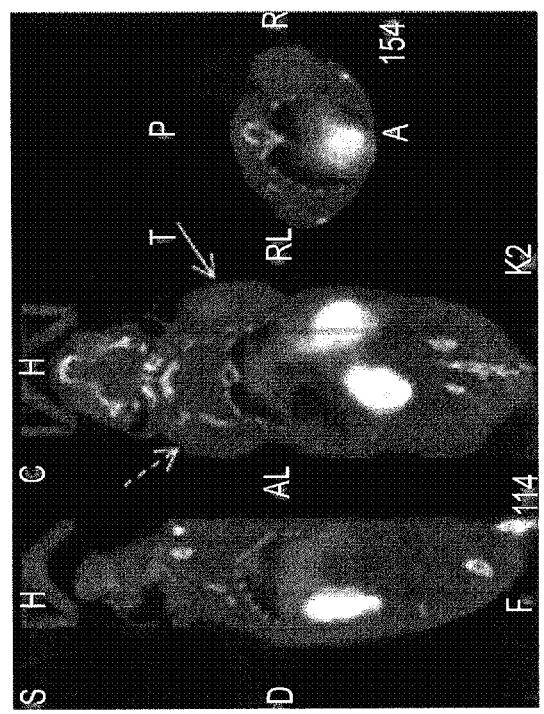

FIG. 5—Three dimensional imaging of radiolabelled D25p in vivo.

The figure in panel (a) represents a representative mouse at the one-hour time point, post injection. The three images represent three different viewing angles—the sagittal (left), coronal (middle) and axial (right). More radioactive tumour uptake was localized in the αvβ6 positive tumour (indicated with solid arrow) than in the αvβ6 negative tumour (indicated with the dashed arrow). Quantitative data showing the average radioactive dose of the three tested mice per gram of tumour at the 1 h, 4 h and 24 h time points are shown in the histogram (b).

Figure 6:
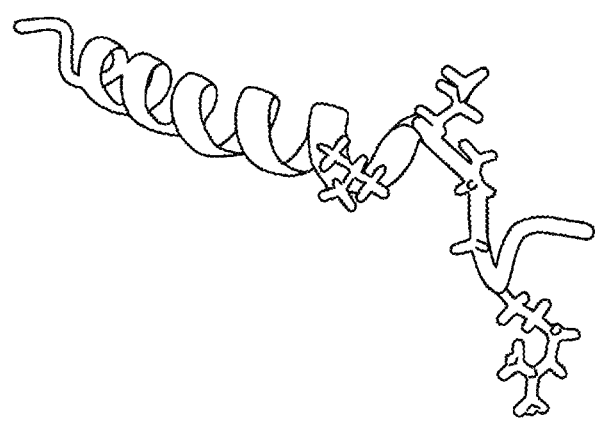
Figure 6:
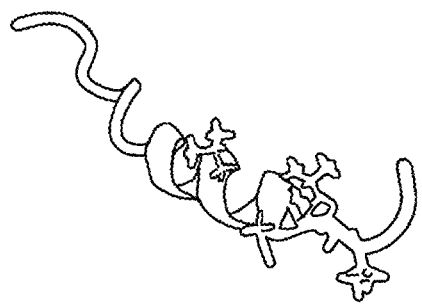

FIG. 6—NMR Structure of D25p and D34p.

3D-rendering model for each peptide based on the mean of 20 NMR structures. Both peptides exhibited the RGD-helix-hairpin motif. D34 which has 22 amino-acids has a shorter helix than peptide D25, which has 29 amino-acids. Helices for both peptides were defined as standard α-helix with the D34 α-helix running from Leu6-Leu17 and D25 α-helix running from Leu6-Gln25.

Figure 7:
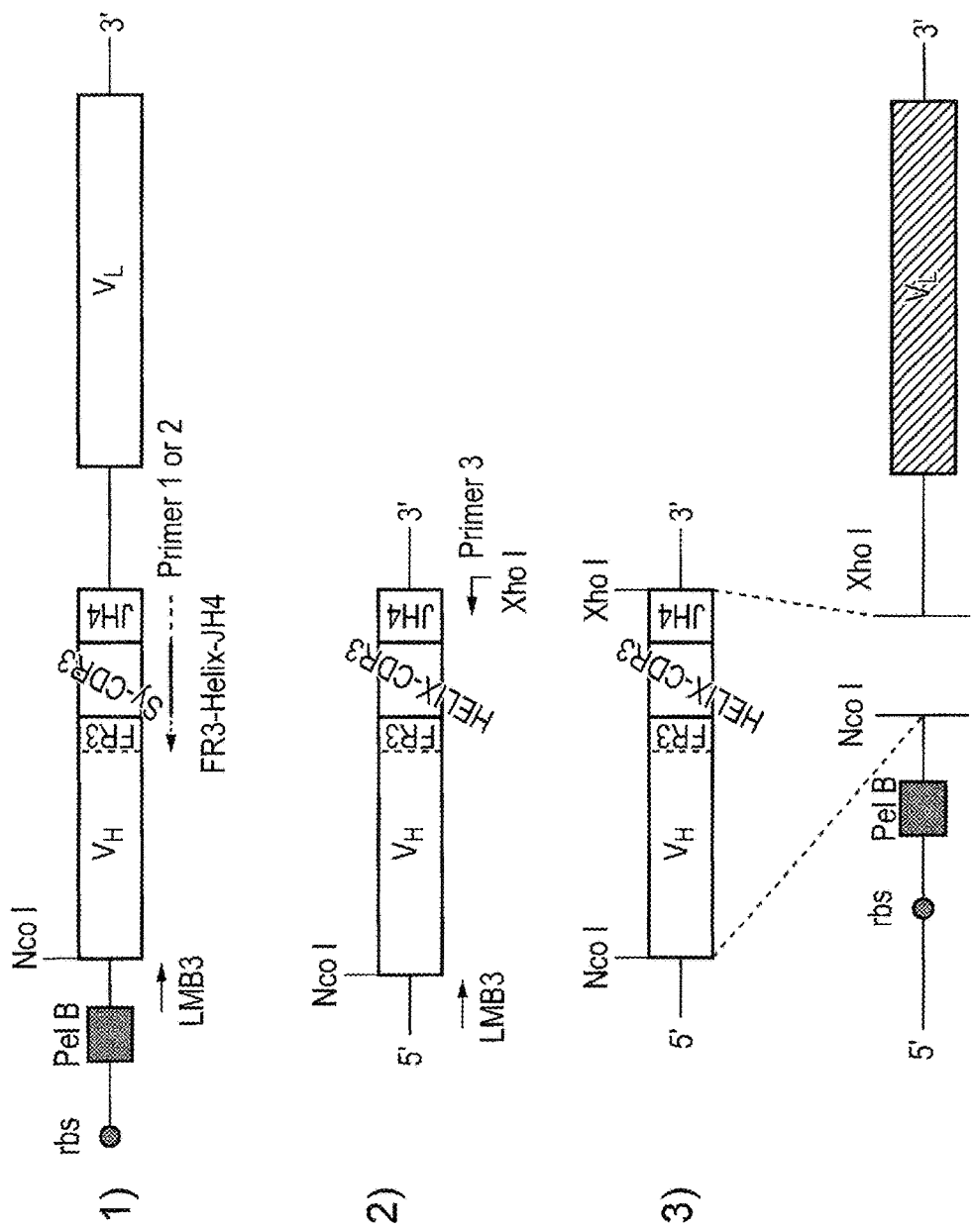

FIG. 7—Cloning strategy used to construct the α- and $3_{10}$-helix $V_H$-CDR3 of scFv phage display libraries.

1) Using the pHEN1 plasmid backbone as the PCR template the $V_H$-CDR3 gene was amplified with the primers LMB3 and the Primer 1 or 2 that includes the FR3, flanked by the α- or $3_{10}$-helix algorithms (respectively) and followed by JH4 sequences.
2) To incorporate a unique Xho1 restriction site, the PCR products derived from step 1 were amplified with LMB3 and Primer 3.

The resultant PCR products from step 2 were digested with Nco1 and Xho1 for insertion into the pIT2 plasmid backbone that contain light chain repertoire.

Figure 8:
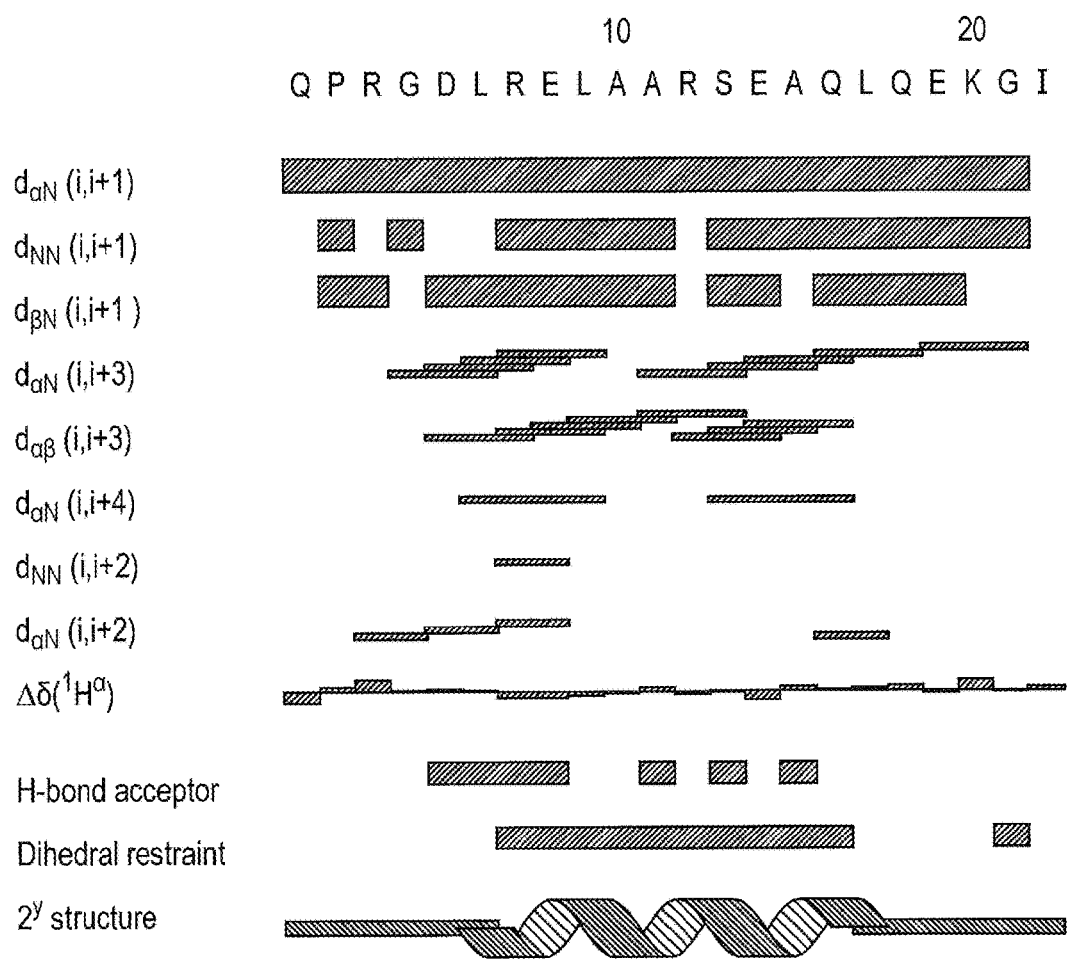

FIG. 8—NOE contacts, chemical shift difference, hydrogen bond donors and Dihedral restraints for D34p peptide with 30% w/v TFE. The secondary structure shown beneath the restraints indicates the limits of helix formation according to Ramachandran analysis of the final 20 structure ensemble.

Figure 9:
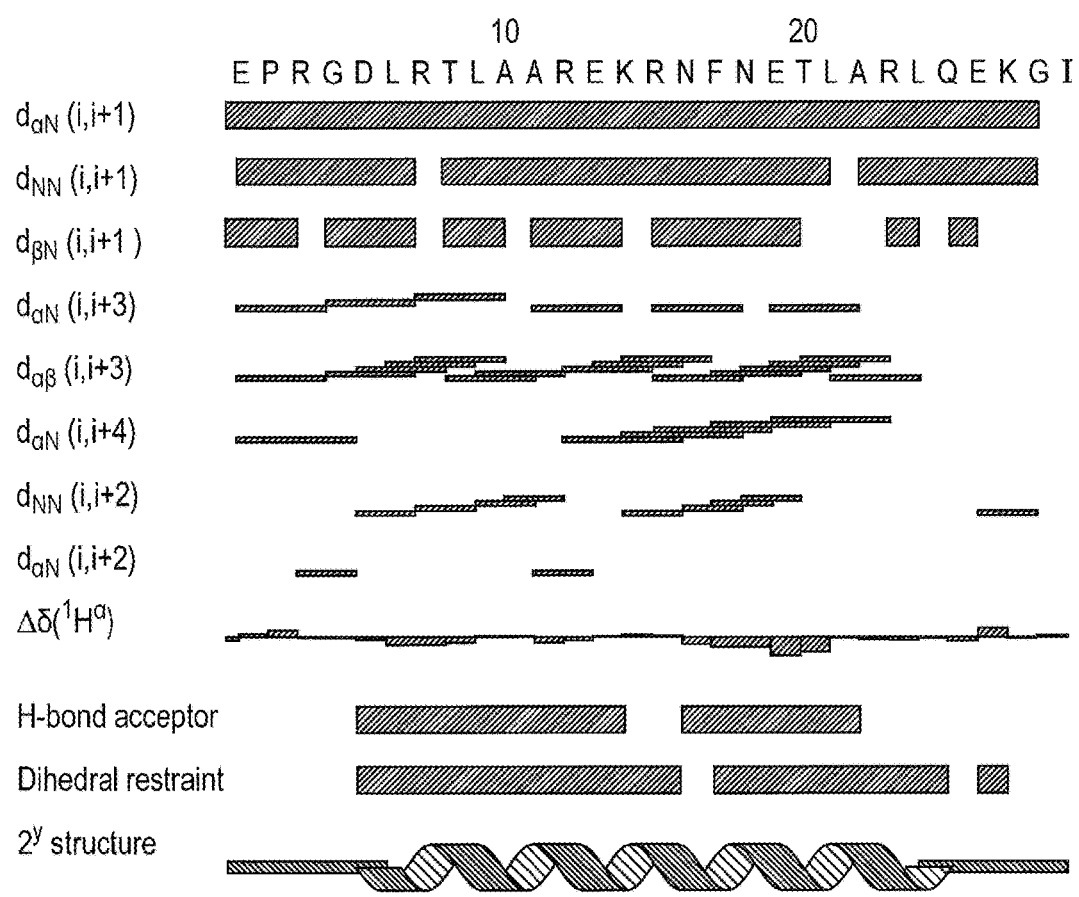

FIG. 9—NOE contacts, chemical shift difference, hydrogen bond donors and Dihedral restraints for D29p peptide in 30% w/v TFE. The secondary structure shown beneath the restraints indicates the limits of helix formation according to Ramachandran analysis of the final 20 structure ensemble.

SUMMARY OF ASPECTS OF THE INVENTION

The present inventors have developed a method for generating an antibody or other affinity reagent library based on the optimal stereochemistry of a ligand:target protein interaction. The method is founded upon the generation of a target-selective library by the incorporation of specific three-dimensional structures into the binding portion of an affinity reagent (for example, the CRD(s) of an antibody). If the specific three-dimensional structures correspond to a ligand:target protein interface the subsequent screening of the library is more likely to generate affinity reagents that will block the ligand:receptor interaction compared to a conventional random library.

As such, in a first aspect the present invention provides a method for generating an affinity reagent library against a target protein which interacts with a ligand, which comprises the following steps;
i) determining one or more structural element(s) of the ligand which are involved in ligand:target protein interaction;
ii) producing a library of peptides which retain these structural element(s); and
iii) grafting each peptide from the library of peptides into a portion of the affinity reagent molecule such that it may interact with the target protein, in order to produce an affinity reagent library.

The affinity reagent may be an antibody or a functional fragment thereof, in which case, in step (iii) of the method the peptide may be grafted in the position of a complementarity determining region (CDR) to produce an antibody library. The CDR may be CDR3. The peptide may be grafted in the place of one, two or all three CDRs in the variable domain of the heavy and/or light chain.

The CDR may be $V_H$—CDR1, $V_H$—CDR2, $V_H$—CDR3, $V_L$—CDR1, $V_L$—CDR2 or $V_L$-CDR3. The method may involve grafting a one or a plurality of peptide libraries into a plurality of CDR positions. The CDR may be CDR3, in particular $V_H$—CDR3.

The affinity reagent may be an antibody mimetic, such as an Affibody, a DARPin, an Anticalin, an Avimer, a Versabody or a Duocalin.

The structural element(s) may be secondary structure features, such as particular α-helix or β-sheet formation. The structural elements may also include key amino acid residues required for the ligand:target protein interaction.

The target protein may be selected from the group of a chemokine, cytokine, growth factor, G-protein coupled receptor (GCPR), tyrosine kinase receptor, an integrin or another class of cell adhesion molecule, a kinase, phosphatase, hydrolase, ubiquitinase, protease, lipase or carbohydrase, an antibody, a structural protein such as actin or myosin, a trafficking protein such as clathrin, a voltage gated ion channel, a ligand gated ion channel, a peptide hormone or a neuropeptide.

The target protein may be αVβ6, wherein the method of the invention comprises the following steps;
i) generating a library of peptides which comprise a hairpin which contains at its turn an RGD motif followed by a C-terminal α-helix or a $3_{10}$-helix; and,
ii) grafting the library of peptides into a portion of the affinity reagent molecule such that it may interact with the target protein, in order to produce an affinity reagent library.

The C-terminal α-helix or $3_{10}$-helix may comprise EP or QP N-terminal and/or LQEKGI (SEQ ID NO: 34)C-terminal capping motifs.

The C-terminal α-helix with EP or QP N-terminal and LQEKGI (SEQ ID NO: 34)C-terminal capping motifs may have the sequence;

(SEQ ID NO. 1)
$E_1P_2R_3G_4D_5L_6X_7X_8L_9A_{10}A_{11}R_{12}Z_{13}K_{14}R_{15}Z_{16}F_{17}N_{18}E_{19}Z_{20}L_{21}$
$A_{22}Z_{23}L_{24}Q_{25}E_{26}K_{27}G_{28}I_{29}$ wherein X and Z are random amino acid residues.

The $3_{10}$-helix with EP N-terminal and LQEKGI (SEQ ID NO: 34)C-terminal capping motifs may have the sequence;

(SEQ ID NO. 2)
$E_1P_2R_3G_4D_5L_6X_7X_8L_9A_{10}A_{11}Z_{12}L_{13}K_{14}Z_{15}E_{16}F_{17}Z_{18}E_{19}N_{20}Z_{21}$
$L_{22}A_{23}Z_{24}L_{25}Q_{26}E_{27}K_{28}G_{29}I_{30}$ wherein X and Z are random amino acid residues.

In a second aspect the present invention provides a method for selecting an affinity reagent capable of binding to a target protein, which method comprises the step of making an affinity reagent library against the target protein by the method according to the first aspect of the invention and screening the library for binding to the target protein.

In a third aspect the present invention provides a peptide comprising the amino acid sequence shown as SEQ ID NO: 23 or SEQ ID NO: 31 or a variant thereof. The variant may, for example, have one or more amino acid insertions, deletions or substitutions. The variant may have 5 or fewer, 4 or fewer, 3 or fewer, 2 or 1 amino acid mutations.

In a fourth aspect the present invention provides αvβ6 antibody comprising a $V_H$-CDR3 sequence comprising a peptide according the third aspect of the invention. An antibody comprising a variant peptide should retain the capacity to interact with αVβ6. An antibody comprising a variant peptide may be capable of inhibiting αvβ6 binding to a peptide such as the A20FMDV2 peptide (NAVPNL-RGDLQVLAQKVART (SEQ ID NO: 3)). An antibody comprising a variant peptide may be capable of inhibiting αVβ6-dependent adhesion of carcinoma cells to immobilised fibronectin.

The antibody may be for use in diagnosing or treating a disease.

The disease may be cancer or fibrosis.

The antibody according to the fourth aspect of the invention may be conjugated to a detectable and/or therapeutic agent.

The method described above provides a more efficient system for the generation of specific antibodies for therapy and research.

DETAILED DESCRIPTION

Affinity Reagent Library
In a first aspect the present invention provides a method for generating an affinity reagent library.

The affinity reagent may be any entity which displays (or can be engineered to display) a target-protein binding site. The target protein-binding site should be displayed in a configuration suitable for binding to the target protein i.e. on an external surface of the molecule.

The affinity reagent may be or comprise a peptide or polypeptide.

The affinity reagent may be an antibody or a functional fragment thereof, or an antibody mimetic.

As used herein, "antibody" means a polypeptide having an antigen binding site which comprises at least one complementarity determining region CDR. The antibody may comprise 3 CDRs and have an antigen binding site which is equivalent to that of a domain antibody (dAb). The antibody may comprise 6 CDRs and have an antigen binding site which is equivalent to that of a classical antibody molecule. The remainder of the polypeptide may be any sequence which provides a suitable scaffold for the antigen binding site and displays it in an appropriate manner for it to bind the antigen. The antibody may be a whole immunoglobulin molecule or a part thereof such as a Fab, F(ab)'$_2$, Fv, single chain Fv (ScFv) fragment or Nanobody. The antibody may be a conjugate of the antibody and another agent or antibody, for example the antibody may be conjugated to a polymer (eg PEG), toxin or label. The antibody may be a bifunctional antibody. The antibody may be non-human, chimeric, humanised or fully human.

The term "antibody library" refers to collection of antibodies that comprise distinct CDRs and thus demonstrate differential specificity.

A typical antibody is composed of two immunoglobulin (Ig) heavy chains and two Ig light chains. Several different types of heavy chain exist that define the class or isotype of an antibody. There are five types of mammalian immunoglobulin heavy chain: γ, δ, α, μ and ε which define the classes of immunoglobulins: IgG, IgD, IgA, IgM and IgE respectively. All heavy chains contain a series of Ig domains, usually with one variable domain ($V_H$) that is important for binding antigen and several constant domains ($C_H1$, $C_H2$, etc.).

There are two types of light chain in mammals, kappa (κ) chain, encoded by the Ig kappa locus (IGK) on human chromosome 2 and lambda (λ) chain, encoded by the Ig lambda locus (IGL) on human chromosome 22. Only one type of light chain is present in a typical antibody, thus the two light chains of an individual antibody are identical. Each light chain is composed of two tandem Ig domains; on constant ($C_L$) domain and one variable domain ($V_L$) that is important for binding antigen.

Binding of the antibody to the antigen is facilitated by the Fab (fragment, antigen binding) region at the N-terminal domain of the antibody. The Fab is composed of one constant and one variable domain from each heavy and light chain of the antibody. The diversity of the antibody repertoire is based on the somatic recombination of variable (V), diversity (D) and joining (J) gene segments. In humans, Ig genes are randomly assembled from about 50 V, 25 D and 6 J gene segments for heavy chains and over 30 potentially functional Vκ and Vλ, light chain genes and 5 Jκ and 4 Jλ, genes, respectively.

Variable loops, three each on the $V_L$ and $V_H$ chains are responsible for binding to the antigen. These loops are referred to as the complementarity determining regions (CDRs). The CDRs (CDR1, CDR2 and CDR3) of each of the $V_H$ and $V_L$ are arranged non-consecutively. Within the variable domain, CDR1 and CDR2 are found in the V region of the polypeptide chain, and CDR3 includes some of V, all of D (heavy chains only) and J regions. Since most sequence variation associated with immunoglobulins is found in the CDRs, these regions may be referred to as hypervariable regions. Among these, CDR3 shows the greatest variability as it is encoded by a recombination of the VJ in the case of a light chain region and VDJ in the case of heavy chain regions. Regions between CDRs in the variable domain of an immunoglobulin are known as framework regions. These are important for establishing the structure of the $V_H$ and $V_L$ domains. The variable domains of the H ($V_H$) and L ($V_L$) chains constitute an Fv unit and can interact closely to form a single chain Fv (ScFv) unit.

The C-terminal domain of an antibody is called the constant region. In most H chains, a hinge region is found. This hinge region is flexible and allows the Fab binding regions to move freely relative to the rest of the molecule. The hinge region is also the place on the molecule most susceptible to the action of proteases which can split the antibody into the antigen binding site (Fab) and the effector (Fc) region.

The domain structure of the antibody molecule is favourable to protein engineering, facilitating the exchange between molecules of functional domains carrying antigen-binding activities (Fabs and Fvs) or effector functions (Fcs). The structure of the antibody also makes it easy to produce antibodies with an antigen recognition capacity joined to molecules such as toxins, lymphocytes, growth factors and detectable or therapeutic agents.

Chimeric antibodies may be produced by transplanting antibody variable domains from one species (for example, a mouse) onto antibody constant domains from another species (for example a human).

Fab, Fv and ScFv fragments with $V_H$ and $V_L$ joined by a polypeptide linker exhibit specificities and affinities for antigen similar to the original monoclonal antibodies. The ScFv fusion proteins can be produced with a non-antibody molecule attached to either the amino or the carboxy terminus. In these molecules, the Fv can be used for specific targeting of the attached molecule to a cell expressing the appropriate antigen. Bifunctional antibodies can also be created by engineering two different binding specificities into a single antibody chain. Bifunctional Fab, Fv and ScFv antibodies may comprise engineered domains such as CDR grafted or humanised domains.

Genes encoding immunoglobulins or immunoglobulin-like molecules can be expressed in a variety of heterologous expression systems. Large glycosylated proteins including immunoglobulins are efficiently secreted and assembled from eukaryotic cells, particularly mammalian cells. Small, non-glycosylated fragments such as Fab, Fv or scFv fragments can be produced in functional form in mammalian cells or bacterial cells.

The antigen-binding domain may be comprised of the heavy and light chains of an immunoglobulin, expressed from separate genes, or may use the light chain of an immunoglobulin and a truncated heavy chain to form a Fab and a F(ab)'$_2$ fragment. Alternatively, truncated forms of both heavy and light chains may be used which assemble to form a Fv fragment. An engineered svFv fragment may also be used, in which case, only a single gene is required to encode the antigen-binding domain.

The affinity reagent may alternatively be a molecule which is not derived from or based on an immunoglobulin. A number of "antibody mimetic" designed repeat proteins (DRPs) have been developed to exploit the binding abilities of non-antibody polypeptides.

Repeat proteins such as ankyrin or leucine-rich repeat proteins are ubiquitous binding molecules which occur, unlike antibodies, intra- and extracellularly. Their unique modular architecture features repeating structural units (repeats), which stack together to form elongated repeat domains displaying variable and modular target-binding surfaces. Based on this modularity, combinatorial libraries of polypeptides with highly diversified binding specificities can be generated. DARPins (Designed Ankyrin Repeat Proteins) are one example of an antibody mimetic based on this technology.

For Anticalins, the binding specificity is derived from lipocalins, a family of proteins which perform a range of functions in vivo associated with physiological transport and storage of chemically sensitive or insoluble compounds. Lipocalins have a robust intrinsic structure comprising a highly conserved β-barrel which supports four loops at one terminus of the protein. These loops for the entrance to a binding pocket and conformational differences in this part of the molecule account for the variation in binding specificity between different lipocalins.

Avimers are evolved from a large family of human extracellular receptor domains by in vitro exon shuffling and phage display, generating multi-domain proteins with binding and inhibitory properties.

Versabodies are small proteins of 3-5 kDa with >15% cysteines which form a high disulfide density scaffold, replacing the hydrophobic core present in most proteins. The replacement of a large number of hydrophobic amino acids, comprising the hydrophobic core, with a small number of disulphides results in a protein that is smaller, more hydrophilic, more resistant to proteases and heat and has a lower density of T-cell epitopes. All four of these proerties result in a protein having considerably reduced immunogenicity. They may also be manufactured in *E. coli*, and are highly soluble and stable.

Structural Features

The overall structure of a protein is provided by primary, secondary and tertiary structural features.

The primary structure of a protein is the linear sequence of its amino acid units.

The secondary structure of a protein is the general three-dimensional form of local segments of amino acid units. Secondary structure in proteins consists of local inter-residue interactions which may be mediated by hydrogen bonds. The most common secondary structures are α-helices and β-sheets. Other helices, such as the $3_{10}$ helix and π helix may also occur. Other extended structures such as the polyproline helix and α-sheet are rare in native state proteins but may represent important protein folding intermediates. Tight turns and loose, flexible loops link the more defined secondary structure elements. The random coil is not a true secondary structure, but is the class of conformations that indicate an absence of regular secondary structure.

Amino acids vary in their ability to form the various secondary structure elements. Proline and glycine are sometimes known as "helix breakers" because they disrupt the regularity of the α-helical backbone conformation; however, both have unusual conformational abilities and are commonly found in turns. Amino acids that prefer to adopt helical conformations in proteins include methionine, alanine, leucine, glutamate and lysine. By contrast, the large aromatic residues such as tryptophan, tyrosine and phenylalanine and $C^\beta$-branched amino acids such as isoleucine, valine and threonine more commonly occur in β-strand conformations. However, these preferences are not strong enough to produce a reliable method of predicting secondary structure from sequence alone.

There are several methods for defining protein secondary structure known in the art (e.g. DEFINE, DSSP, STRIDE and SST).

Tertiary structure is the three-dimensional structure of a protein formed by the packing of secondary structure elements into compact globular units known as protein domains. Whole proteins can comprise one or several such domains, and tertiary structure can refer to each individual domain as well as to the complete configuration of the whole protein, provided it contains a single, contiguous polypeptide chain backbone. The tertiary structure of a protein is primarily determined by hydrophobic interactions and the formation of disulphide bonds between cysteine residues.

Proteins that are formed by the assembly of separate, folded polypeptide chains give rise to quaternary structure.

As described above, the ability of an affinity reagent, such as an antibody, to bind an antigen or target protein is conferred primarily by the sequence and secondary structure of the antigen-binding site. Where the affinity reagent is an antibody or fragment the ability to bind an antigen or target protein is conferred primarily by the sequence and secondary structure of the CDR loops, principally CDR3. The method of the present invention therefore involves determining peptide structures which enable a ligand to bind to a target protein, generating a library of peptides which mimic these structural features and grafting the peptides into the antigen-binding site of affinity reagents. For example, the peptides may be grafted into the one or more of the CDR regions of antibodies.

Methods for determining the structural features required for a ligand to bind to a target protein are known in the art. Such methods include, but are not limited to, Macromolecular crystallography, Nuclear magnetic resonance spectroscopy of proteins, Electron paramagnetic resonance (EPR) or electron spin resonance (ESR) spectroscopy, Cryo-electron microscopy.

Once the structural features involved in the ligand:target protein interaction have been determined these are used to guide the generation of peptide libraries comprising the requisite structural features. The peptides are then grafted into the antigen-binding site of affinity reagents e.g. the CDR(s) of an antibody.

In this regard, an algorithm may be used which utilise the known properties of amino acids to generate a range of possible peptides which will provide the required secondary structural features.

In addition to the amino acids which provide the required structural features, further amino acids may be incorporated into the peptides in order to generate diversity within the peptide library. Alternative amino acids with similar properties may be utilised to provide the required structural features. This use of alternative amino acids with similar properties will introduce further diversity into the peptide library.

Methods for grafting peptides into the antigen-binding site of affinity reagents are known in the art. For example when "grafting" a peptide into the CDR region of an antibody, this may involve inserting a nucleotide sequence encoding the peptide into the CDR region of an antibody. Alternatively "grafting" may involve replacing the endogenous CDR encoding nucleotide sequence with one which encodes a peptide providing the required structural features.

As described above, the antigen specificity of an antibody is primarily determined by the CDR3 region. The method of the present invention may therefore involve grafting the peptide library into the CDR3-encoding region of an antibody.

The CDR3 region may be $V_L$—CDR3 or $V_H$—CDR3.

Target Protein

The term 'target protein' refers to the entity against which the affinity reagent library is designed.

The term protein, as used herein, is synonymous with peptide or polypeptide.

These terms are used in the conventional sense to mean a series of residues, typically L-amino acids, connected one to the other, typically by peptide bonds between the α-amino and carboxyl groups of adjacent amino acids.

The target protein may be, but is not limited to, a chemokine, cytokine or growth factor, a G-protein coupled receptor (GCPR) or tyrosine kinase receptor, an integrin or another class of cell adhesion molecule, an enzyme such as a kinase, phosphatase, hydrolase, ubiquitinase, protease, lipase or carbohydrase; the target protein may also be an antibody, a structural protein such as actin or myosin, a trafficking protein such as clathrin or an ion channel (voltage gated or ligand gated); the target protein may also be a peptide hormone, for example insulin or a thyroid hormone or a neuropeptide.

Integrin Alpha-V/Beta 6 (AVB6)

In one aspect, the present invention provides a method for generating an affinity reagent library against αVβ6.

Integrins are obligate heterodimers containing two distinct chains, called the α and β subunits. Eighteen α and eight β subunits have been characterized in mammals and the α and β subunits each penetrate the plasma membrane and possess small cytoplasmic domains.

αVβ6 is a receptor for various ligands including fibronectin, tenascin, and the latency-associated peptide-1 and latency-associated peptide-3 (LAP1 and LAP3), the $NH_2$-terminal region of the latent precursor form of TGF-β1 and TGF-β3. αVβ6 recognizes the RGD motif in its ligands and internalisation of αVβ6 via clathrin-mediated endocytosis promotes carcinoma cell invasion. αVβ6 binds to foot-and-mouth disease virus (FMDV) VP1 protein, coxsackievirus A9 and coxsackievirus B1 capsid proteins and acts as a receptor for these viruses.

The expression of αVβ6 is restricted primarily to epithelial cells where it is expressed at relatively low levels in healthy tissue and significantly up-regulated during development, injury, wound healing, and in epithelial tumours. αVβ6 is a tumour-selective target that is expressed on a variety of cancer cells, including epithelial malignancies such oral squamous carcinoma, cervical carcinoma, colon cancer and non-small cell lung cancer. It has been shown to promote cancer cell migration, invasion and growth in vivo. Strong expression of αVβ6 correlates with poor progression in multiple cancers.

The method of generating an affinity reagent library against αVβ6 involves generating a library of peptides which comprise a hairpin which contains at its turn an RGD motif followed by a C-terminal α-helix or a $3_{10}$-helix.

An "RGD motif" is a tripeptide of Arg-Gly-Asp.

An "α-helix" is a right-handed coil, in which every backbone N—H group donates a hydrogen bond to the backbone C=O group of the amino acid four residues earlier. This secondary structure is also sometimes called a classic Pauling-Corey-Branson alpha helix or a $4_{13}$-helix. Among types of local structure in proteins, the α-helix is the most regular and the most predictable from sequence, as well as the most prevalent.

It is known in the art that different amino-acid sequences have different propensities for forming an α-helical structure. Methionine, alanine, leucine, uncharged glutamine and lysine all have especially high helix-forming propensities, whereas proline and glycine have poor helix-forming propensities. Proline either breaks or kinks a helix, both because it cannot donate an amide hydrogen bond (having no amide hydrogen), and also because its sidechain interferes sterically with the backbone of the preceding turn, this forces a bend of about 30° in the helix axis. However, proline is often seen as the first residue of a helix, due to its structural rigidity. At the other extreme, glycine also tends to disrupt helices because its high conformational flexibility makes it entropically expensive to adopt the relatively constrained α-helical structure.

Table 1 shows the estimated differences in free energy, estimated in kcal/mol per residue in an alpha-helical configuration, relative to Alanine arbitrarily set as zero. Higher numbers (more positive free energies) are less favoured. Deviations from these average numbers are possible, depending on the identities of the neighbouring residues.

TABLE 1

| Amino Acid | 3-Letter | 1-Letter | Helical Propensity |
|---|---|---|---|
| Alanine | Ala | A | 0.0 |
| Arginine | Arg | R | 0.21 |
| Asparagine | Asn | N | 0.65 |
| Aspartic acid | Asp | D | 0.69 |
| Cysteine | Cys | C | 0.68 |
| Glutamic acid | Glu | E | 0.40 |
| Glutamine | Gln | Q | 0.39 |
| Glycine | Gly | G | 1 |
| Histidine | His | H | 0.61 |
| Isoleucine | Ile | I | 0.41 |
| Leucine | Leu | L | 0.21 |
| Lysine | Lys | K | 0.26 |
| Methionine | Met | M | 0.24 |
| Phenylalanine | Phe | F | 0.54 |
| Proline | Pro | P | 3.16 |
| Serine | Ser | S | 0.5 |
| Threonine | Thr | T | 0.66 |
| Tryptophan | Trp | W | 0.49 |
| Tyrosine | Tyr | Y | 0.53 |
| Valine | Val | V | 0.61 |

A $3_{10}$-helix a right-handed helical structure. Each amino acid corresponds to a 120° turn in the helix (i.e., the helix has three residues per turn), and a translation of 2.0 Å (=0.2 nm) along the helical axis, and has 10 atoms in the ring formed by making the hydrogen bond. The N—H group of an amino acid forms a hydrogen bond with the C=O group of the amino acid three residues earlier.

A helix has an overall dipole moment caused by the aggregate effect of all the individual dipoles from the carbonyl groups of the peptide bond pointing along the helix axis. This can lead to destabilization of the helix through entropic effects. As a result, helices may be capped at the N-terminal end by a negatively charged amino acid, such as glutamate, in order to neutralize this helix dipole. C-terminal capping with a positively charged amino acid, such as lysine, may also occur. The N-terminal positive charge is commonly used to bind negatively charged ligands such as phosphate groups, which is especially effective because the backbone amides can serve as hydrogen bond donors.

The helix may comprise an N and/or C-terminal capping motif. For example the helix may comprise a Glu-Pro N-terminal and/or Leu-Gln-Glu-Lys-Gly-Ile (SEQ ID NO: 34)C-terminal capping motif.

Affinity Reagent Selection

The present invention also provides a method for selecting an affinity reagent which is capable of binding to a target protein from a library generated as described herein.

The affinity reagent library may be expressed in a prokaryotic or eukaryotic system.

Methods for the identification of affinity reagents capable of binding to a target protein are well known in the art and include, but are not limited to, ELISA, western blot, FACS/flow cytometry, surface plasma resonance, protease protection assays and FRET.

Affinity Reagents

The present invention also provides peptide sequences and affinity reagents comprising said peptide sequences.

Peptide sequences provided by the present invention, which comprise an RGD motif followed by a C-terminal α-helix or 3₁₀-helix are shown in Table 2. A20 FMDV, a known ligand of αVβ6, is also shown for comparison.

The length of the α-helix sequences may be increased by the use of multiple units of the L to $L_{16}$ or $A_{17}$ monomer sequence.

For example the α-helix sequence may be (LXXLAARZKRZFNEZL)$_n$ (SEQ ID NO: 35) or (LXXLAARZKRZFNEZLA)$_n$ (SEQ ID NO: 36).

*wherein Z=any amino acid

The peptide sequence may be D25p: EPRGDLRTLAAREKRNFNETLARLQEKGI (SEQ ID NO: 23)

The peptide sequence may be D34p: QPRGDLRELAARSEAQLQEKGI (SEQ ID NO: 31).

The present invention also provides an affinity reagent which comprises a peptide selected from the above list within its target protein-binding site. The affinity reagent may be an antibody comprising a peptide selected from the above list within its CDR region.

The antibody may comprise SEQ ID NO: 23 or SEQ ID NO: 31 in its CDR region.

The CDR region may be CDR3.

The CDR region may be V$_H$—CDR3.

An affinity reagent of the present invention may be conjugated to, for example, a toxin, a detectable agent and/or a therapeutic agent.

A "toxin" is a poison produced by a living cell or organism. Examples of toxins include, but are not limited to, cyanotoxins, heamotoxins, necrotoxins, neurotoxins, cytotoxins and myoctoxins.

A "detectable agent" is any entity which enables binding of the affinity reagent to the target protein to be determined. The detectable may include, but is not limited to, a fluorescent protein or maker such as green fluorescent protein or FITC, a radiolabel or an enzyme, for example horse radish peroxidase.

A "therapeutic agent" is any entity which may be useful for the treating of disease. Therapeutic agents include cytokines or haematopoietic factors including, but not limited to, IL-1, IL-2, IL-4, IL-5, IL-13, IL-6, CSF-1, M-CSF, GM-CSF, IFNα, IFNβ, IFNγ, IL-10, IL-12, VEGF, bone morphogenic proteins, FGFs, TNF and TGFβ.

Therapeutic agents also include chemotherapeutic agents. A chemotherapeutic agent contemplated includes, without limitation, alkylating agents, nitrosoureas, ethylenimines/methylmelamine, alkyl sulfonates, antimetabolites, pyrimidine analogs, epipodophylotoxins, enzymes such as L-asparaginase; biological response modifiers such as IFNα, IL-2, G-CSF and GM-CSF; platinium coordination complexes such as cisplatin and carboplatin, anthracenediones, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

TABLE 2

| | | |
|---|---|---|
| A20FMDV | NAVPNLRGDLQVLAQKVART | (SEQ ID NO. 3) |
| RGD/3.10 helix | RGDLXXLAAZLKZEFZENZLAZ | (SEQ ID NO. 4) |
| RGD/Alpha helix | RGDLXXLAARZKRZFNEZLAZ | (SEQ ID NO. 5) |
| D1 | QPRGDLTSLAATLKTEFMENTLPRLQEKGI | (SEQ ID NO. 6) |
| D2 | EPRGDLQRLAARINPVFQRDASPRLQEKGI | (SEQ ID NO. 7) |
| D4 | QPRGDLQDLAARNKRTFNESLARLQEKGI | (SEQ ID NO. 8) |
| D6 | QPRGDLKGLQEKGI | (SEQ ID NO. 9) |
| D7 | EPRGDLRNLAARVKREFNENLAALQEKGI | (SEQ ID NO. 10) |
| D9 | QPRGDLHLLAARSKPGSNEMLATLQEKGI | (SEQ ID NO. 11) |
| D13 | QPRGDLHMLAARAKRHFNEMLATLQEKGI | (SEQ ID NO. 12) |
| D14 | EPRGDLQMLAARLKKEFTENQLAPLQEKGI | (SEQ ID NO. 13) |
| D15 | QPRGDLTSLAATLKTEFMENTLPRLQEKGI | (SEQ ID NO. 14) |
| D17 | QPRGDLASLAPRPKPFFNETLASLQEKGI | (SEQ ID NO. 15) |
| D18 | EPRGDLSSLAARTKPGVQPAALATLQEKGI | (SEQ ID NO. 16) |
| D19 | EPRGDLQILATPERTGLSTLQEKGI | (SEQ ID NO. 17) |
| D20 | SAREPRGDLSPLAARAKREFNENLANLQEKGI | (SEQ ID NO. 18) |
| D21/D4 | QPRGDLQDLAARNKRTFNESLARLQEKGI | (SEQ ID NO. 19) |
| D22 | EPRGDLQRLAARINPVFQRDASPRLQEKGI | (SEQ ID NO. 20) |
| D23 | EPRGDLQALAARTKRDFNEVLPPLQEKGI | (SEQ ID NO. 21) |
| D24 | QPRGDLDILAARIKRDFNQSLASLQEKGI | (SEQ ID NO. 22) |
| D25 | EPRGDLRTLAAREKRNFNETLARLQEKGI | (SEQ ID NO. 23) |
| D26 | EPRGDLHSLAARTKRGFNEKRLAHLQEKGI | (SEQ ID NO. 24) |

TABLE 2-continued

| | | |
|---|---|---|
| D27 | EPRGDLQSLASPTLQEKGI | (SEQ ID NO. 25) |
| D28 | QPRGDLHVLASPPLQEKGI | (SEQ ID NO. 26) |
| D29 | EPRGDLSRLAARSKRDFNQELAALQEKGI | (SEQ ID NO. 27) |
| D30 | EPRGDLHQLAARSKLQEKGI | (SEQ ID NO. 28) |
| D31 | QPRGDLSSLAPRGKPDFNETLARLQEKGI | (SEQ ID NO. 29) |
| D32 | EPRGDLWQLAARWKRPSTSSLAMLQEKGI | (SEQ ID NO. 30) |
| D34 | QPRGDLRELAARSEAQLQEKGI | (SEQ ID NO. 31) |
| D35 | EPRGDLASLAARYKPEFNEQLAYLQEKGI | (SEQ ID NO. 32) |
| N38 | EPRGDLQMLAARLKKEFTENQLAPLQEKGI | (SEQ ID NO. 33) |

Diagnosing or Treating a Disease

An affinity reagent of the present invention may be used for the diagnosis of a disease. Herein the affinity reagent may be administered to a subject who may have or is suspected of having a disease which is associated with the expression of the target protein. Preferably the target protein is not expressed, or is expressed to a lesser degree, on non-diseased cells and tissues.

An affinity reagent of the present invention may be used for the prevention of disease through use as a prophylactic entity. Herein the affinity reagent may be administered to a subject who has not yet contracted the disease and/or who is not showing any symptoms of the disease to prevent or impair the cause of the disease or to reduce or prevent development of at least one symptom associated with the disease.

An affinity reagent of the present invention may be used for the treatment of a disease through use as a therapeutic entity. Herein the affinity reagent may be administered to a subject having an existing disease or condition in order to lessen, reduce or improve at least one symptom associated with the disease and/or to slow down, reduce or block the progression of the disease.

The invention will now be further described by way of Examples, which are meant to serve to assist one of ordinary skill in the art in carrying out the invention and are not intended in any way to limit the scope of the invention.

EXAMPLES

Example 1—Library Design

A structural selectivity was introduced to a phage display library by genetically encoding the three-dimensional (3D) αVβ6 ligand recognition motif (RGD-helix-hairpin) into the antibody binding pocket at the VH-CDR3. FIG. 1a shows the amino-acid sequence identity and mean NMR solution structure of A20FMDV2, a 20mer peptide ($N_1A_2V_3P_4N_5L_6R_7G_8D_9L_{10}Q_{11}V_{12}L_{13}A_{14}Q_{15}K_{16}V_{17}A_{18}R_{19}T_{20}$) (SEQ ID NO: 3), derived from the foot and mouth disease virus VP1 coat protein, and known to be a highly specific and potent ligand for αVβ6. The peptide includes the RGDLXXL (SEQ ID NO: 37) motif identified previously identified as the minimal motif that maintained specificity for αVβ6. The three-dimensional structure of A20FMDV2 was determined by NMR and comprises a hairpin structure with RGD at the tip of the turn followed by a C-terminal helix. Saturation Transfer Difference NMR analysis of A20FMDV2 when bound to αVβ6 showed that, again, A20FMDV2 formed an RGD-helix structure with $R_7$, $L_{10}$, $L_{13}$ and $K_{16}$ residues bound closest to αVβ6, consistent with a $3_{10}$ helix structure and recently such RGD-helix motif peptides has been shown to exhibit motional characteristics that could influence specificity.

From these data, plus the STD-NMR data (Hazelbag, S. et al. *The Journal of pathology;* 212, 316-324 (2007)), two algorithms were designed to develop VH-CDR3 libraries encoding a hairpin containing at its turn, an RGD motif, followed by a C-terminal α-helix (FIG. 1b) or a $3_{10}$-helix (FIG. 1c); the helical wheel map for each library is also shown. The template synthetic VH-CDR3 was based on the α-helix donor sequence $L_8A_9R_{10}L_{11}K_{12}R_{13}E_{14}F_{15}N_{16}E_{17}$ (SEQ ID NO: 38), which is helix 1 from the *Drosophila* engrailed homeodomain (EN-HD). However in the library the $L_8$ was changed to $A_8$ in order to prevent formation of an LXXLL (SEQ ID NO: 39) motif. The template VH-CDR3 included:

(SEQ ID NO: 1)
$E_1P_2R_3G_4D_5L_6X_7A_8L_9A_{10}A_{11}R_{12}Z_{13}K_{14}R_{15}Z_{16}F_{17}N_{18}E_{19}Z_{20}L_{21}A_{22}Z_{23}L_{24}Q_{25}E_{26}K_{27}G_{28}I_{29}$.

Z and X were random amino-acid residues introduced into the same quadrant as the Leu residues of the RGDLXXL (SEQ ID NO: 37) motif: at position 13, 16, 20 and 23 in the α-helix based on the helical wheel (3.6 residues per pitch turn of helix). The EP and the LQEKGI (SEQ ID NO: 34) motifs were N- and C-terminal helix-capping regions, respectively (based on the standard Schellmann C-cap: Leu-Gln-Glu-Lys-Gly-Ile (LQEKGI) (SEQ ID NO: 34) (FIG. 1b). To extend the helix length further, the EN-HD donor sequence was repeated from positions 21/22 in the library.

To build the $3_{10}$ helix library the $E_1P_2R_3G_4D_5L_6X_7A_8L_9A_{10}A_{11}Z_{12}L_{13}K_{14}Z_{15}E_{16}F_{17}Z_{18}E_{19}N_{20}Z_{21}L_{22}A_{23}Z_{24}L_{25}Q_{26}E_{27}K_{28}G_{29}I_{30}$ (SEQ ID NO: 1) template was used, inserting a random amino acid residue in every third position following the RGDLXXL (SEQ ID NO: 37) motif in the $3_{10}$ helix (3.0 residues per pitch turn of $3_{10}$helix, FIG. 1c). Hence, the random residues automatically provided helices of different lengths because they included helix stabilising residues, such as alanine, lysine or arginine or, alternatively, helix destroying residues such as proline as well as including residues covering all side chain properties to test the effect of charge, hydrophobicity and steric interactions.

Example 2—Library Selection and Screening for Lead Candidates

After 3 rounds of alternate panning on immobilised recombinant αVβ6 and cells expressing αVβ6 it was apparent that the α-helix library performed better with ~80% of screened clones binding to recombinant αVβ6 in ELISA while in the $3_{10}$-helix library we observed only ~15% binders (FIG. 2a). Automated sequencing of 124 strong binders revealed 41 unique VH-CDR3 sequences encoding mostly an α-helix demonstrating that the α-helix is the preferred structure for the αVβ6 interaction. None of the VH-CDR3 sequences matched to any known human proteins and thus represented wholly unique sequences. 33 unique scFv clones were tested by flow cytometry on αVβ6-expressing and αVβ6-negative cell lines (FIG. 2b). None of the scFv bound to the αVβ6-negative cells and many scFv bound well to the αVβ6-expressing cells. Since A375puro endogenously express the RGD directed integrins α5β1, αVβ3, αVβ5 and αVβ8, these data suggest strongly that the scFvs exhibited αVβ6-specific binding. Based upon expression yields, biochemical stability (SDS-PAGE) and strength of binding to cellular αVβ6 (flow cytometry; FIG. 2b) further studies were based on 2 different scFvs from the α-helix library: D25scFv (D25) and D34scFv (D34) (FIG. 2b).

The size-exclusion chromatography profile of the purified D25 scFv showed a main peak eluting at 70 ml, corresponding to the 30 kDa scFv. For D25 a lower peaks eluting at 45-60 ml was also observed, corresponding to scFv dimers and tetramers. (FIG. 2c). The corresponding VH-CDR3 peptides (D25p and D34p, respectively), which exhibited αVβ6-specific binding to cells (FIG. 3a), were also observed.

Example 3—αVβ6-Specific Antagonistic Efficacy

D25scFv, D34scFv, D25p and D34p showed a dose-dependent inhibition of binding to cellular αvβ6 of A20FMDV2 peptide (NAVPNLRGDLQVLAQKVART (SEQ ID NO: 3)) that binds with high affinity ($K_D$ 1.7 nM) and specificity to the αvβ6 integrin (FIG. 3b-c). Additionally, D25scFv, D25p, D34scFv and D34p exhibited significant concentration-dependent inhibition of αVβ6-dependent adhesion of carcinoma cells to immobilised fibronectin (FIGS. 3d and 3e).

Example 4—αVβ6-Specific Internalisation

D25scFv and D34scFv exhibited cellular internalisation in αVβ6-expressing cells but not in αVβ6-negative cells. At 0 minutes, the scFvs were localised at the cell surface (FIGS. 4a, d for D25 and D34, respectively) but after incubation at 37° C. for 45 minutes, they were localised within the cell cytoplasm and nucleus (FIGS. 4.b, e for D25 and D34, respectively). Omitting the scFv primary layer and labelling only with anti-myc and the fluorochrome-labelled secondary antibody showed very little nuclear staining suggesting the nuclear localisation of the scFvs was real (FIGS. 4c, f) for D25 and D34, respectively). Similarly, biotinylated-D25p and biotinylated-D34p also underwent cellular internalisation in αVβ6-expressing cells (FIGS. 4 h and k for D25p and D34p, respectively) but not in αVβ6-negative cells (FIGS. 4 i, and 1 for D25p and D34p, respectively). Efficient internalisation was observed at 30-45 minutes (FIGS. 4 h, k for D25p and D34p, respectively) but no nuclear localisation was observed.

Example 5—Biotinylated-D25 Peptide Localises αVβ6-Expressing Tumours In Vivo

When 12.5MBq of [In111]-DTPA-Streptavidin decorated with biotinylated-D25p was intravenously injected into three mice bearing both a subcutaneous αVβ6-positive A3751136 tumour and an αvβ6-negative A375Ppuro tumour, on opposite shoulders, a 32% injected dose uptake in the αvβ6-positive tumour was observed compared with only 3% for the αvβ6-negative tumour at 1 hour post-injection, a ratio of >10:1 (FIG. 5). This translated into a very clear discrimination of the αVβ6-positive tumour by single-photon emission computed tomography (SPECT) imaging (FIG. 5).

Example 6—Structural Determination of D25 and D34 Peptides by NMR

NMR was used to solve the solution structures for peptides D34p and D25p. FIG. 6 shows the 3D-rendering model closest to the mean calculated for each peptide from an ensemble of 20 NMR structures; the associated structural statistical data from CNS for both peptides is available in Table 4 and NOE and structural contact information is available in FIGS. 8 and 9. Both peptides exhibited the RGD-helix-hairpin motif. D34 which has 22 amino-acids has a shorter helix than peptide D25, which has 29 amino-acids. Helices for both peptides were defined as standard α-helix with the D34 α-helix running from Leu6-Leu17 and D25 α-helix running from Leu6-Gln25.

TABLE 3

Oligonucleotides used to build the structural guided library

| Primer I.D | Sequence (5' to 3') |
|---|---|
| Primer 1 (LMB3) | |
| Primer 2/α-helix | CCAGATCCCTTTCTCCTGCAAMNNGGCTAGM NNCTCGTTGAAMNNCCGCTTMNNTCGGGCTG CGAGMNNMNNTAGGTCTCCTCGAGGTTCTCT TGCACAGTAATACACGGCCGTGTC (SEQ ID NO: 40) |
| Primer 2/310-helix | CCAGATCCCTTTCTCCTGCAAMNNCGCGAGM NNGTTCTCMNNGAACTCMNNCTTCAGMNNGG CTGCGAGMNNMNNTAGGTCTCCTCGAGGTTC TCTTGCACAGTAATACACGGCCGTGTC (SEQ ID NO: 41) |
| Primer 3 | GCCTGAACCGCCTCCACCACTCGAGACGGTG ACCAGGGTACCTTGGCCCCAGATCCCTTTCT CCTGCAA (SEQ ID NO: 42) |
| Fdseq | GAATTTTCTGTATGAGG (SEQ ID NO: 43) |
| LMB3 | CAGGAAACAGCTATGAC (SEQ ID NO: 44) |

TABLE 4

NMR and refinement statistics for 20 structure ensembles of peptides

| | D34p | D25p |
|---|---|---|
| NMR distance and dihedral constraints | | |
| Distance constraints | | |
| Total NOE | 319 | 624 |
| Intra-residue | 115 | 233 |
| Inter-residue | 204 | 391 |
| Sequential (|i − j| = 1) | 123 | 200 |
| Medium-range (|i − j| < 4) | 79 | 189 |
| Long-range (|i − j| > 5) | 2 | 2 |
| Hydrogen bonds | 7 | 15 |
| Dihedral restraints | 22 | 40 |
| Lennard-Jones Energy (kJ mol$^{-1}$) | −890.97 | −1608.67 |
| Structure statistics* | | |
| Violations | | |
| NOE violations >0.2 Å | 0 ± 0.002 | 0 ± 0.007 |
| Dihedral angle violations >2.0° | 0 ± 0.008 | 0 ± 0.007 |
| Ramachandran (%)† | | |
| Most favoured regions | 85.0 | 88.1 |
| Additionally allowed regions | 10.9 | 10.2 |
| Generously allowed regions | 3.5 | 1.0 |

TABLE 4-continued

NMR and refinement statistics for
20 structure ensembles of peptides

|  | D34p | D25p |
|---|---|---|
| Disallowed regions | 0.6 | 0.6 |
| Average pairwise r.m.s. deviation* (Å) | Over residues 6-17 | Over residues 6-25 |
| Heavy | 1.346 | 1.431 |
| Backbone | 0.540 | 0.649 |

*For all accepted structures of 40 structure calculation
[†]For 20 lowest energy water minimised structures Methods Library Construction and Selection Library construction is shown in FIG. 1. A pool of 50 human VH genes cloned into the pHEN1 vector was used as a PCR template. The library initially was amplified with LMB3 primer (Table 3), which anneals to pHEN1 vector sequences 5' to the cloned VH gene and primer 1, which anneals to 3' end of the VH gene which was composed of the frame work 3 (FR3) region, the structurally guided motifs encoded by the α- or $3_{10}$-helix algorithms and finally the JH4 sequences (Table 3). In a second PCR step, XhoI restriction site was introduced 3' to the JH4 sequence after amplification with primer 2 and LMB3. The VH gene amplicons containing inserts encoding the algorithms were then digested with XhoI and NcoI restriction enzymes and inserted into the NcoI and XhoI treated pIT2 vector containing the VL repertoire.

The α-helix and $3_{10}$ libraries were each rescued separately using M13-KO7 helper phage. For selection, we used in parallel each library separately as well as mixed α-helix and $3_{10}$ libraries. The initial phage selection was performed using immobilised recombinant αvβ6 protein. After two rounds of selection on immobilised αvβ6 the libraries were selected on cell-expressed αVβ6 using A375Pβ6 and A375PPuro cell lines, for αVβ6-positive and αVβ6-negative selection, respectively. First line screening was performed using ELISA with 5 μg/ml immobilised recombinant αvβ6 as described.

Cell Lines

The adherent melanoma cell lines A375Pβ6 and A375Ppuro were cultured in Dulbecco's Modified Eagles' Medium (DMEM) supplemented with 10% Foetal Calf Serum (FCS). The human oral squamous cell carcinoma VB6, which was engineered to express high levels of αvβ6, was grown in Keratinocyte Growth Medium.

Screening for Integrin Specificity by Flow Cytometry

Purified scFv were tested for specificity for αVβ6 by flow cytometry using the isogenic pairs of cell lines, A375P136 and A375Ppuro, which express similar levels of four RGD-binding integrins (αVβ3, αVβ5, αVβ8, α5β1) but only A3751β6 express αVβ6. Briefly, cells were detached with trypsin/EDTA, rinsed twice in ice-cold wash buffer (0.1% BSA/DMEM/0.1% $NaN_3$) and $2 \times 10^5$ cells re-suspended in 50 μl of wash buffer per sample. In between all incubation steps, all samples were washed twice with wash buffer unless otherwise stated. Cells were incubated on ice for 1 hr with 0.1 or 1 uM purified scFv of peptide, washed twice. For scFv, cells were then incubated for 1 hr on ice with mouse anti-Myc antibody (clone 9E10, Santa Cruz) at 1:100. After washing, bound antibody was detected with anti-mouse IgG-Alexaflour 488 (1:250 for 1 h; Molecular Probes), on ice. Bound VH-CDR3 derived peptide were detected by rabbit anti-biotin IgG (1:200), followed by anti-rabbit IgG-Alexafluor 488 (1:250; Molecular Probes). Cells were analysed using the FACSCalibur (Beckton Dickinson). Cell expression of αVβ6 integrin was detected with mouse monoclonal antibody (clone 10D5, 10 μg/ml; Millipore) and non-specific (control) binding with non-immune class matched IgG.

Inhibition of αVβ6 Ligand Binding

The scFv lead candidates propensity to inhibit binding of the αVβ6-specific biotinylated-A20FMDV2 to αVβ6 expressing cells was determined by pre-incubation with purified scFv or peptide (0.1 and 1.0 μM) for 10 mins, immediately followed by 40 mins incubation with the biotinylated A20FMDV2 (10 nM). Bound A20FMDV2 peptides were detected by rabbit anti-biotin IgG (1:200), followed by anti-rabbit IgG-Alexafluor 488 (1:250; Molecular Probes).

Fast Protein Liquid Chromatography (FPLC)

The structural stability of scFv proteins was assessed by gel filtration chromatography using a HiPrep 16/60 sephacryl S-200 (GE healthcare, Amersham, UK) connected to an AKTA FPLC (GE healthcare, Amersham, UK). Fractionations were performed in PBS at a flow rate of 0.3 ml/min with detection at 280 nm. A Calibration Kit (GE healthcare, Amersham, UK) containing protein markers (aprotinin, ribonuclease A, carbonic anhydrase, ovalbumin and conalbumin) was used to generate a calibration curve. Equal amounts of each of the protein markers were prepared to 500 μl in PBS prior to loading onto the column. Kav values derived from the equation: $Kav=(V_e-V_0)/(V_c-V_0)$; where Ve=elution volume, Vc=geometric column volume, and V0=column void volume were plotted against log molecular weight to generate a protein calibration curve. Purified scFv (50 ug/500 ul) was loaded onto the gel filtration column and molecular weight of the different peaks was determined using the calibration curve.

Internalisation Assay

In 24-well culture plates, $2 \times 10^4$ cells (DX3puro, DX3β6 or VB6) were seeded onto 13 mm diameter glass coverslips and allowed to incubate overnight at 37° C. in growth medium. Cells were washed thwice in serum free medium (SFM) and then scFv (4 uM) or biotinylated-CDR3-peptide (100 nM) diluted in SFM added on ice for 10 mins. After two ice-cold washes and a further 10 mins on ice with mouse anti-biotin antibody (10 ug/ml) pre-warmed media containing 10% FCS was added to the cells and incubated at 37° C. At 10 min intervals between 0-60 mins, cells were fixed in 2% HCHO in PBS and permeabilised with 0.1% TritonX-100 (PBS) for 3 mins. scFv was detected with mouse anti c-myc (1:100 dilution, clone 9E10; 30 mins, ambient temperature) and followed by while peptides were detected by rabbit anti-biotin IgG (1:200). Both peptide and scFv detected with anti-mouse Alexa488 for 30'. Nuclei were counter-labelled with 4',6-diamidino-2-phenylindole (DAPI), coverslips mounted with Mowiol and samples examined by confocal microscopy (Zeiss LSM510, Welwyn Garden City).

Picogreen Adhesion Assay

All adhesion assays were performed in quadruplicate and repeated at least 2-3 times. In a 96-well plate format, test wells were coated with Fibronectin (10 ug/ml/PBS) and negative control wells were coated with 0.1% BSA (bovine serum albumin)/PBS. After incubation at 37° C. for 1 hour, plates were washed in PBS thwice and blocked with 0.1% BSA/PBS for 30 mins at 37° C. Following a PBS rinse, cells were seeded into the wells, the plate resting on ice to avoid dehydration and to ensure an initial uniform temperature for the experiment. Purified scFv or peptide was added (25 ul) to the wells at the desired concentrations, before adding $1.5 \times 10^4$ cells (25 ul) per well. In some experiments, cells ($1.5\times10^4$) were pre-treated with β1 blocking antibody AIIB2 at 10 ug/ml before seeding into test wells. To determine percentage adhesion, standard curves were generated by plating $0$-$2.5\times10^4$ cells in separate wells. After incubating plates at 37° C. for 30' plates were washed twice in 1 mM $CaCl_2$/0.5 mM $MgCl_2$/PBS and transferred into −80° C. for 15 mins. Adherent cells were quantified using a Picogreen kit (Invitrogen) and analysed on a fluorescence reader (FLUOstar Optima, BMG Labtech Ltd, Bucks, UK).

In Vivo Localization

Biotinylated-peptide was radiolabelled with Indium-111. To 10 ug of DOTA-Biotin (Macrocyclics.com #C-100) buffered in 1M Ammonium Acetate (pH 5.5) was added Indium[$^{111}$In]-acetate. The mixture was heated to 80° C. for 30 mins and cooled at RT for 10 mins. The labelled DOTA-Biotin was added to streptavidin at a 1:1 Molar Ratio (1 mg of streptavidin per 17.6 ug of Dota-Biotin). To this mixture, 88 ug of botinylated-D25p was added and 10 ul of the mixture analysed by size exclusion-HPLC to verify the stability of radiolabelled products pre- and post-labelling. A total of 50MBq was used to label 25 ug of peptide; the sample was divided into four such that each mouse received 12.5 MBq (6.25 ug) of 111In-labelled D25 peptide.

Female athymic nude mice were subcutaneously injected with 1000 ($2\times10^6$ cells) of A3731β6 into the right shoulder and A375puro in the left shoulder. Tumours were allowed to develop for 20 days and 200 µl of freshly radiolabelled $^{111}$In-labelled D25 peptide was administered intravenously. Tumours were imaged by NanoSPECT/CT (Bioscan, Inc) at 1 hr, 4 hr and 24 hr-time points as follows: Mice were placed onto the imaging bed and initial low resolution CT scans were collected at 45KVp, 180 projections per rotation, 500 ms per projection. Subsequently SPECT images were acquired (45 minutes acquisition time) and data reconstructed using on-board HiSPECT-NG software (Bioscan). To measure radioactivity associated with tumours the Nano-SPECT/CT machine was calibrated (before the experiment) by imaging a phantom with an Indium-111 standard solution. Subsequently Invivoscope software (Invicro) was used to generate three-dimensional regions of Interest (ROI) around the tumours and the ROIs converted to megabequerels Structural Determination by NMR Study Solution NMR structures of peptides D25 and D34 on 0.1% TFE were solved as previously. All NMR data for peptides A22(D25p) and A29 (D34p) were obtained at 283 K from a 14.1 T (600 MHz $^1$H) Bruker Avance III NMR spectrometer equipped with a 5 mm QCI-F cryoprobe. All NMR samples were 350 µL within a Shigemi NMR tube and contained 1 mM peptide in 25 mM sodium phosphate buffer at pH 6.5 also containing 50 mM sodium chloride, 4% (v/v) dimethylsulfoxide (DMSO), and 30% (v/v) trifluroethanol-d3 (TFE). NMR data processing was completed using TopSpin 3.1 (Bruker), assignments were completed using CCPN Analysis.

$^1$H chemical shifts and through-space structural assignments were obtained from two-dimensional TOCSY and NOESY NMR experiments with mixing times of 20 ms/60 ms for TOCSY and 250 ms for NOESY. The observed NOE contacts support the presence of an α-helical conformation along the length of the peptide with NOEs observed between Hα and HN (i−i+3) as well as Hα and Hβ (i−i+3). Structural ensembles were calculated using CNS and including dihedral angles confirmed by DANGLE analysis and predicted hydrogen-bond donor acceptor pairs. The final ensemble was water-minimised using YASARA Structure software and Ramachandran analysis of each peptide ensemble was completed using PROCHECK-NMR.

The invention claimed is:

1. A method for generating an affinity reagent library against a target protein which interacts with a ligand, wherein the target protein is αVβ6, and wherein the method comprises:
   i) generating a library of peptides which comprise:
   a hairpin which contains, at its turn, an RGD motif;
   an α-helix or a 3$_{10}$-helix located C-terminal to the hairpin; and
   a LQEKGI (SEQ. ID NO: 34) C-terminal capping motif; and
   ii) grafting each peptide from the library of peptides into a portion of the affinity reagent molecule such that it may interact with the target protein, in order to produce an affinity reagent library.

2. A method according to claim 1, wherein the affinity reagent is an antibody or a functional fragment thereof.

3. A method according to claim 2, wherein in step (ii) the peptide is grafted in the position of a complementarity determining region (CDR) to produce an antibody library.

4. A method according to claim 3, wherein the CDR is CDR3.

5. A method according to claim 1, wherein the affinity reagent is an antibody mimetic.

6. A method according to claim 5, wherein the antibody mimetic is an Affibody, a DARPin, an Anticalin, an Avimer, a Versabody or a Duocalin.

7. A method according to claim 1, wherein the peptide further comprises an EP N-terminal capping motif.

8. A method according to claim 1, wherein the peptide comprises the sequence:

$E_1P_2R_3G_4D_5L_6X_7X_8L_9A_{10}A_{11}R_{12}Z_{13}K_{14}R_{15}Z_{16}F_{17}N_{18}E_{19}Z_{20}L_{21}A_{22}Z_{23}L_{24}Q_{25}E_{26}K_{27}G_{28}I_{29}$ (SEQ ID NO: 1)

wherein X and Z are random amino acid residues.

9. A method according to claim 1, wherein the peptide comprises the sequence:

$E_1P_2R_3G_4D_5L_6X_7X_8L_9A_{10}A_{11}Z_{12}L_{13}K_{14}Z_{15}E_{16}F_{17}Z_{18}E_{19}N_{20}Z_{21}L_{22}A_{23}Z_{24}L_{25}Q_{26}E_{27}K_{28}G_{29}I_{30}$ (SEQ ID NO: 2)

wherein X and Z are random amino acid residues.

10. A method for selecting an affinity reagent capable of binding to an αVβ6 protein, which comprises the step of making an affinity reagent library against the αVβ6 protein by a method according to claim 1 and screening the library for binding to the αVβ6 protein.

11. A peptide comprising the amino acid sequence shown as SEQ ID NO: 23 or SEQ ID NO: 31.

12. An αVβ6 antibody comprising a $V_H$-CDR3 sequence comprising a peptide according to claim 11.

13. A method of diagnosing or treating a disease comprising administering to a subject an antibody according to claim 12.

14. A method according to claim 13, wherein the disease is cancer.

15. An antibody according to claim 12, wherein the antibody is conjugated to a detectable and/or therapeutic agent.

16. A method according to claim 13, wherein the antibody is conjugated to a detectable and/or therapeutic agent.

17. A method according to claim 1, wherein the affinity reagent is a single chain fragment variable (scFv).

* * * * *

```
                      SEQUENCE LISTING

<160> NUMBER OF SEQ ID NOS: 44

<210> SEQ ID NO 1
<211> LENGTH: 29
<212> TYPE: PRT
<213> ORGANISM: Artificial Sequence
<220> FEATURE:
<223> OTHER INFORMATION: C-terminal alpha-helix sequence
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid

<400> SEQUENCE: 1

Glu Pro Arg Gly Asp Leu Xaa Xaa Leu Ala Ala Arg Xaa Lys Arg Xaa
1               5                   10                  15

Phe Asn Glu Xaa Leu Ala Xaa Leu Gln Glu Lys Gly Ile
                20                  25
```

```
<210> SEQ ID NO 2
<211> LENGTH: 30
<212> TYPE: PRT
<213> ORGANISM: Artificial Sequence
<220> FEATURE:
<223> OTHER INFORMATION: 3(10)-helix sequence
<220> FEATURE:
<221> NAME/KEY: misc_feature
<222> LOCATION: (7)..(8)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid

<400> SEQUENCE: 2

Glu Pro Arg Gly Asp Leu Xaa Xaa Leu Ala Ala Xaa Leu Lys Xaa Glu
1               5                   10                  15

Phe Xaa Glu Asn Xaa Leu Ala Xaa Leu Gln Glu Lys Gly Ile
            20                  25                  30

<210> SEQ ID NO 3
<211> LENGTH: 20
<212> TYPE: PRT
<213> ORGANISM: Artificial Sequence
<220> FEATURE:
<223> OTHER INFORMATION: A20 FMDV ligand sequence

<400> SEQUENCE: 3

Asn Ala Val Pro Asn Leu Arg Gly Asp Leu Gln Val Leu Ala Gln Lys
1               5                   10                  15

Val Ala Arg Thr
            20

<210> SEQ ID NO 4
<211> LENGTH: 22
<212> TYPE: PRT
<213> ORGANISM: Artificial Sequence
<220> FEATURE:
<223> OTHER INFORMATION: Peptide sequence comprising RGD motif followed
      by a C-terminal 3(10)-helix
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
```

```
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 4

Arg Gly Asp Leu Xaa Xaa Leu Ala Ala Xaa Leu Lys Xaa Glu Phe Xaa
1               5                   10                  15

Glu Asn Xaa Leu Ala Xaa
            20

<210> SEQ ID NO 5
<211> LENGTH: 21
<212> TYPE: PRT
<213> ORGANISM: Artificial Sequence
<220> FEATURE:
<223> OTHER INFORMATION: Peptide sequence comprising RGD motif followed
      by a C-terminal alpha-helix
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid

<400> SEQUENCE: 5

Arg Gly Asp Leu Xaa Xaa Leu Ala Ala Arg Xaa Lys Arg Xaa Phe Asn
1               5                   10                  15

Glu Xaa Leu Ala Xaa
            20

<210> SEQ ID NO 6
<211> LENGTH: 30
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 6

Gln Pro Arg Gly Asp Leu Thr Ser Leu Ala Ala Thr Leu Lys Thr Glu
1               5                   10                  15

Phe Met Glu Asn Thr Leu Pro Arg Leu Gln Glu Lys Gly Ile
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix
```

```
<400> SEQUENCE: 7

Glu Pro Arg Gly Asp Leu Gln Arg Leu Ala Ala Arg Ile Asn Pro Val
1               5                   10                  15

Phe Gln Arg Asp Ala Ser Pro Arg Leu Gln Glu Lys Gly Ile
            20                  25                  30

<210> SEQ ID NO 8
<211> LENGTH: 29
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 8

Gln Pro Arg Gly Asp Leu Gln Asp Leu Ala Ala Arg Asn Lys Arg Thr
1               5                   10                  15

Phe Asn Glu Ser Leu Ala Arg Leu Gln Glu Lys Gly Ile
            20                  25

<210> SEQ ID NO 9
<211> LENGTH: 14
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 9

Gln Pro Arg Gly Asp Leu Lys Gly Leu Gln Glu Lys Gly Ile
1               5                   10

<210> SEQ ID NO 10
<211> LENGTH: 29
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 10

Glu Pro Arg Gly Asp Leu Arg Asn Leu Ala Ala Arg Val Lys Arg Glu
1               5                   10                  15

Phe Asn Glu Asn Leu Ala Ala Leu Gln Glu Lys Gly Ile
            20                  25

<210> SEQ ID NO 11
<211> LENGTH: 29
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 11

Gln Pro Arg Gly Asp Leu His Leu Leu Ala Ala Arg Ser Lys Pro Gly
1               5                   10                  15

Ser Asn Glu Met Leu Ala Thr Leu Gln Glu Lys Gly Ile
            20                  25

<210> SEQ ID NO 12
<211> LENGTH: 29
<212> TYPE: PRT
<213> ORGANISM: Artificial Sequence
```

```
<220> FEATURE:
<223> OTHER INFORMATION: Peptide sequence comprising RGD motif followed
      by a C-terminal alpha-helix or 3(10)-helix

<400> SEQUENCE: 12

Gln Pro Arg Gly Asp Leu His Met Leu Ala Ala Arg Ala Lys Arg His
1               5                   10                  15

Phe Asn Glu Met Leu Ala Thr Leu Gln Glu Lys Gly Ile
            20                  25

<210> SEQ ID NO 13
<211> LENGTH: 30
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 13

Glu Pro Arg Gly Asp Leu Gln Met Leu Ala Ala Arg Leu Lys Lys Glu
1               5                   10                  15

Phe Thr Glu Asn Gln Leu Ala Pro Leu Gln Glu Lys Gly Ile
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 14

Gln Pro Arg Gly Asp Leu Thr Ser Leu Ala Ala Thr Leu Lys Thr Glu
1               5                   10                  15

Phe Met Glu Asn Thr Leu Pro Arg Leu Gln Glu Lys Gly Ile
            20                  25                  30

<210> SEQ ID NO 15
<211> LENGTH: 29
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 15

Gln Pro Arg Gly Asp Leu Ala Ser Leu Ala Pro Arg Pro Lys Pro Phe
1               5                   10                  15

Phe Asn Glu Thr Leu Ala Ser Leu Gln Glu Lys Gly Ile
            20                  25

<210> SEQ ID NO 16
<211> LENGTH: 30
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 16

Glu Pro Arg Gly Asp Leu Ser Ser Leu Ala Ala Arg Thr Lys Pro Gly
1               5                   10                  15

Val Gln Pro Ala Ala Leu Ala Thr Leu Gln Glu Lys Gly Ile
            20                  25                  30
```

```
<210> SEQ ID NO 17
<211> LENGTH: 25
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 17

Glu Pro Arg Gly Asp Leu Gln Ile Leu Ala Thr Pro Glu Arg Thr Gly
1               5                   10                  15

Leu Ser Thr Leu Gln Glu Lys Gly Ile
            20                  25

<210> SEQ ID NO 18
<211> LENGTH: 32
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 18

Ser Ala Arg Glu Pro Arg Gly Asp Leu Ser Pro Leu Ala Ala Arg Ala
1               5                   10                  15

Lys Arg Glu Phe Asn Glu Asn Leu Ala Asn Leu Gln Glu Lys Gly Ile
            20                  25                  30

<210> SEQ ID NO 19
<211> LENGTH: 29
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 19

Gln Pro Arg Gly Asp Leu Gln Asp Leu Ala Ala Arg Asn Lys Arg Thr
1               5                   10                  15

Phe Asn Glu Ser Leu Ala Arg Leu Gln Glu Lys Gly Ile
            20                  25

<210> SEQ ID NO 20
<211> LENGTH: 30
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 20

Glu Pro Arg Gly Asp Leu Gln Arg Leu Ala Ala Arg Ile Asn Pro Val
1               5                   10                  15

Phe Gln Arg Asp Ala Ser Pro Arg Leu Gln Glu Lys Gly Ile
            20                  25                  30

<210> SEQ ID NO 21
<211> LENGTH: 29
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix
```

```
<400> SEQUENCE: 21

Glu Pro Arg Gly Asp Leu Gln Ala Leu Ala Ala Arg Thr Lys Arg Asp
1               5                   10                  15

Phe Asn Glu Val Leu Pro Pro Leu Gln Glu Lys Gly Ile
            20                  25

<210> SEQ ID NO 22
<211> LENGTH: 29
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 22

Gln Pro Arg Gly Asp Leu Asp Ile Leu Ala Ala Arg Ile Lys Arg Asp
1               5                   10                  15

Phe Asn Gln Ser Leu Ala Ser Leu Gln Glu Lys Gly Ile
            20                  25

<210> SEQ ID NO 23
<211> LENGTH: 29
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 23

Glu Pro Arg Gly Asp Leu Arg Thr Leu Ala Ala Arg Glu Lys Arg Asn
1               5                   10                  15

Phe Asn Glu Thr Leu Ala Arg Leu Gln Glu Lys Gly Ile
            20                  25

<210> SEQ ID NO 24
<211> LENGTH: 30
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 24

Glu Pro Arg Gly Asp Leu His Ser Leu Ala Ala Arg Thr Lys Arg Gly
1               5                   10                  15

Phe Asn Glu Lys Arg Leu Ala His Leu Gln Glu Lys Gly Ile
            20                  25                  30

<210> SEQ ID NO 25
<211> LENGTH: 19
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 25

Glu Pro Arg Gly Asp Leu Gln Ser Leu Ala Ser Pro Thr Leu Gln Glu
1               5                   10                  15

Lys Gly Ile
```

```
<210> SEQ ID NO 26
<211> LENGTH: 19
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 26

Gln Pro Arg Gly Asp Leu His Val Leu Ala Ser Pro Pro Leu Gln Glu
1               5                   10                  15

Lys Gly Ile

<210> SEQ ID NO 27
<211> LENGTH: 29
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 27

Glu Pro Arg Gly Asp Leu Ser Arg Leu Ala Ala Arg Ser Lys Arg Asp
1               5                   10                  15

Phe Asn Gln Glu Leu Ala Ala Leu Gln Glu Lys Gly Ile
            20                  25

<210> SEQ ID NO 28
<211> LENGTH: 20
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 28

Glu Pro Arg Gly Asp Leu His Gln Leu Ala Ala Arg Ser Lys Leu Gln
1               5                   10                  15

Glu Lys Gly Ile
            20

<210> SEQ ID NO 29
<211> LENGTH: 29
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 29

Gln Pro Arg Gly Asp Leu Ser Ser Leu Ala Pro Arg Gly Lys Pro Asp
1               5                   10                  15

Phe Asn Glu Thr Leu Ala Arg Leu Gln Glu Lys Gly Ile
            20                  25

<210> SEQ ID NO 30
<211> LENGTH: 29
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix
```

```
<400> SEQUENCE: 30

Glu Pro Arg Gly Asp Leu Trp Gln Leu Ala Ala Arg Trp Lys Arg Pro
1               5                   10                  15

Ser Thr Ser Ser Leu Ala Met Leu Gln Glu Lys Gly Ile
            20                  25

<210> SEQ ID NO 31
<211> LENGTH: 22
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 31

Gln Pro Arg Gly Asp Leu Arg Glu Leu Ala Ala Arg Ser Glu Ala Gln
1               5                   10                  15

Leu Gln Glu Lys Gly Ile
            20

<210> SEQ ID NO 32
<211> LENGTH: 29
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 32

Glu Pro Arg Gly Asp Leu Ala Ser Leu Ala Ala Arg Tyr Lys Pro Glu
1               5                   10                  15

Phe Asn Glu Gln Leu Ala Tyr Leu Gln Glu Lys Gly Ile
            20                  25

<210> SEQ ID NO 33
<211> LENGTH: 30
<212> TYPE: PRT
<213> ORGANISM: Artificial Sequence
<220> FEATURE:
<223> OTHER INFORMATION: Peptide sequence comprising RGD motif followed
      by a C-terminal alpha-helix or 3(10)-helix

<400> SEQUENCE: 33

Glu Pro Arg Gly Asp Leu Gln Met Leu Ala Ala Arg Leu Lys Lys Glu
1               5                   10                  15

Phe Thr Glu Asn Gln Leu Ala Pro Leu Gln Glu Lys Gly Ile
            20                  25                  30

<210> SEQ ID NO 34
<211> LENGTH: 6
<212> TYPE: PRT
<213> ORGANISM: Artificial Sequence
<220> FEATURE:
<223> OTHER INFORMATION: C-terminal capping motif

<400> SEQUENCE: 34

Leu Gln Glu Lys Gly Ile
1               5

<210> SEQ ID NO 35
<211> LENGTH: 16
<212> TYPE: PRT
<213> ORGANISM: Artificial Sequence
<220> FEATURE:
<223> OTHER INFORMATION: alpha-helix sequence
```

```
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 35

Leu Xaa Xaa Leu Ala Ala Arg Xaa Lys Arg Xaa Phe Asn Glu Xaa Leu
1               5                   10                  15

<210> SEQ ID NO 36
<211> LENGTH: 17
<212> TYPE: PRT
<213> ORGANISM: Artificial Sequence
<220> FEATURE:
<223> OTHER INFORMATION: alpha-helix sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 36

Leu Xaa Xaa Leu Ala Ala Arg Xaa Lys Arg Xaa Phe Asn Glu Xaa Leu
1               5                   10                  15

Ala

<210> SEQ ID NO 37
<211> LENGTH: 7
<212> TYPE: PRT
<213> ORGANISM: Artificial Sequence
<220> FEATURE:
<223> OTHER INFORMATION: Peptide motif
<220> FEATURE:
<221> NAME/KEY: misc_feature
<222> LOCATION: (5)..(6)
<223> OTHER INFORMATION: Xaa can be any naturally occurring amino acid

<400> SEQUENCE: 37

Arg Gly Asp Leu Xaa Xaa Leu
1               5

<210> SEQ ID NO 38
<211> LENGTH: 10
<212> TYPE: PRT
<213> ORGANISM: Artificial Sequence
<220> FEATURE:
<223> OTHER INFORMATION: Alpha-helix donor sequence
```

<400> SEQUENCE: 38

Leu Ala Arg Leu Lys Arg Glu Phe Asn Glu
1               5                   10

<210> SEQ ID NO 39
<211> LENGTH: 5
<212> TYPE: PRT
<213> ORGANISM: Artificial Sequence
<220> FEATURE:
<223> OTHER INFORMATION: Sequence motif
<220> FEATURE:
<221> NAME/KEY: misc_feature
<222> LOCATION: (2)..(3)
<223> OTHER INFORMATION: Xaa can be any naturally occurring amino acid

<400> SEQUENCE: 39

Leu Xaa Xaa Leu Leu
1               5

<210> SEQ ID NO 40
<211> LENGTH: 117
<212> TYPE: DNA
<213> ORGANISM: Artificial Sequence
<220> FEATURE:
<223> OTHER INFORMATION: Primer 2/alpha-helix
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t

<400> SEQUENCE: 40
ccagatccct ttctcctgca amnnggctag mnnctcgttg aamnnccgct tmnntcgggc       60
tgcgagmnnm nntaggtctc ctcgaggttc tcttgcacag taatacacgg ccgtgtc        117

<210> SEQ ID NO 41
<211> LENGTH: 120
<212> TYPE: DNA
<213> ORGANISM: Artificial Sequence
<220> FEATURE:
<223> OTHER INFORMATION: Primer 2/310-helix
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t

```
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t

<400> SEQUENCE: 41
ccagatccct ttctcctgca amnncgcgag mnngttctcm nngaactcmn ncttcagmnn      60
ggctgcgagm nnmnntaggt ctcctcgagg ttctcttgca cagtaataca cggccgtgtc    120

<210> SEQ ID NO 42
<211> LENGTH: 69
<212> TYPE: DNA
<213> ORGANISM: Artificial Sequence
<220> FEATURE:
<223> OTHER INFORMATION: Primer 3

<400> SEQUENCE: 42
gcctgaaccg cctccaccac tcgagacggt gaccagggta ccttggcccc agatcccttt     60
ctcctgcaa                                                            69

<210> SEQ ID NO 43
<211> LENGTH: 17
<212> TYPE: DNA
<213> ORGANISM: Artificial Sequence
<220> FEATURE:
<223> OTHER INFORMATION: Primer Fdseq

<400> SEQUENCE: 43
gaattttctg tatgagg                                                   17

<210> SEQ ID NO 44
<211> LENGTH: 17
<212> TYPE: DNA
<213> ORGANISM: Artificial Sequence
<220> FEATURE:
<223> OTHER INFORMATION: Primer LMB3

<400> SEQUENCE: 44
caggaaacag ctatgac                                                   17
```